United States Patent [19]
Bell et al.

[11] Patent Number: 5,436,155
[45] Date of Patent: Jul. 25, 1995

[54] ISOLATED DNA ENCODING A SOMATOSTATIN RECEPTOR

[75] Inventors: Graeme I. Bell, Chicago, Ill.; Yuichiro Yamada, Osaka; Susumu Seino, Chiba, both of Japan

[73] Assignee: Arch Development Corporation, Chicago, Ill.

[21] Appl. No.: 816,283

[22] Filed: Dec. 31, 1991

[51] Int. Cl.$^6$ .................. C07K 14/71; C12N 15/12
[52] U.S. Cl. ................... 435/252.3; 435/69.1; 435/320.1; 530/350; 536/23.5; 536/24.31
[58] Field of Search ............... 435/69.1, 257.3, 320.1; 536/27, 23.5, 24.31; 530/350

[56] References Cited

U.S. PATENT DOCUMENTS 4,859,609  8/1989  Dull et al. .................. 436/501

OTHER PUBLICATIONS

J. Biol. Chem. 264:18789–95 (Nov. 1989) Reyl-Desmars et al. Solubilization and Immunopurification of a Somatostatin Receptor from Human Gastric Tumoral Cell Line HGT-1*.
P.N.A.S. 83:599–603 (Feb. 1986) Ferretti et al. Total synthesis of a gene for bovine rhodopsin.
Meth. in Enzym. 91:399–413, (1983) Hunkapiller et al. High–Sensitivity Sequencing with a Gas–Phase Sequenator.
P.N.A.S. vol. 86; 1480–1484, Mar. 1989, He et al. Purification of a putative brain somatostatin receptor.
Nature vol. 311, 626–631, 18 Oct. 1984, Leonard et al. Molecular cloning and expression of cDNAs for human interleukin-2 receptor.
Nature vol. 313; 806–810, 28 Feb. 1985, Jacobs et al. Isolation and characterization of genome and cDNA clones of human erythropoietin.
Stephanie Rens–Domiano, et al; "Biochemical and Functional Properties of Somatostatin Receptors"; Journal of Neurochemistry, vol. 58, No. 6, pp. 1987–1996.
Meyerhof et al.,"Cloning of a cDNA Encoding a Novel Putative G–Protein–Coupled Receptor Expressed in Specific Rat Brain Regions," DNA and Cell Biology, vol. 10:689–694 (1991).
"Octreotide Steaming Ahead," The Lancet, vol. 339:837–839 (Apr. 4, 1992).

Primary Examiner—Garnette D. Draper
Assistant Examiner—John D. Ulm
Attorney, Agent, or Firm—Arnold, White & Durkee

[57] ABSTRACT

The invention relates generally to compositions of and methods for obtaining somatostatin receptors. The invention relates as well to the DNA sequences encoding somatostatin receptors, the recombinant vectors carrying those sequences, the recombinant host cells including either the sequences or vectors, and recombinant somatostatin receptor polypeptides. By way of example, the invention discloses the cloning and functional expression of at least three different somatostatin receptors, SSTR1, SSTR2 and SSTR3 from two different mammalian sources. The invention includes as well, methods for using the isolated, recombinant receptor polypeptides in assays designed to select and improve substances capable of interacting with somatostatin receptor polypeptides for use in diagnostic, drug design and therapeutic applications.

42 Claims, 13 Drawing Sheets

```
                                                        1
                                    Met Phe Pro Asn Gly Thr Ala Ser Ser Pro Ser Pro
                                    ATG TTC CCC AAT GGC ACC GCC TCC TCT CCT CCC AGC CCG
                                                        10
                                                                              Ser                    40
       Gly Ser Cys Gly Glu Gly       Ala Cys                                                    Gly Met Glu Glu
CCCCCTCAGCTGCG                        Gly Gly Ser Arg Gly Pro Ala Ala Ala Asp Gly Met Glu Glu
       GGC AGC TGC GGC GAA           GGC GGC AGC AGG GGC CCC GCC GCT GCG GAC GGC ATG GAG GAG
              20                                         30
                                                                                        60
       Pro Gly Arg Asn Ala Ser Gln Asn Gly Thr Leu Ser Glu Gly Gln Gly Ser Ala Ile Leu Ile Ser
       CCA GGG CGA AAT GCG TCC CAG AAC GGG ACC TTG AGC GAG GGC CAG GGC AGC GCC ATC CTG ATC TCT

Phe Ile Tyr Ser Val Val Cys Leu Val Gly Leu Cys Gly Asn Ser Met Val Ile Tyr Val Ile Leu
       TTC ATC TAC TCC GTG GTG TGC CTG GTG GGG CTG TGT GGG AAC TCT ATG GTG ATC TAC GTG ATC CTG
                                            70                              80
                90                                         100
       Arg Tyr Ala Lys Met Lys Thr Ala Thr Asn Ile Tyr Ile Leu Asn Leu Ala Ile Ala Asp Glu Leu
       CGC TAT GCC AAG ATG AAG ACG GCC ACC AAC ATC TAC ATC CTA AAT CTG GCC ATT GCT GAT GAG CTG
                                                                        120
       Leu Met Leu Ser Val Pro Phe Leu Val Thr Ser Thr Leu Leu Arg His Trp Pro Phe Gly Ala Leu
       CTC ATG CTC AGC GTG CCC TTC CTA GTC ACC TCC ACG TTG CGC CAC TGG CCC TTC GGT GCG CTG
                                                                                        150
       Leu Cys Arg Leu Val Leu Ser Val Asp Ala Val Asn Met Phe Thr Ser Ile Tyr Cys Leu Thr Val
       CTC TGC CGC CTC GTC AGC GTG GAC GCG GTC AAC ATG TTC ACC AGC ATC TAC TGT CTG ACT GTG
              130                                  140
                                                  160                              170
       Leu Ser Val Asp Arg Tyr Val Ala Val His Pro Ile Lys Ala Ala Arg Tyr Arg Pro Thr
       CTC AGC GTG GAC CGC TAC GTG GCC GTG CAT CCC ATC AAG GCG GCC CGC TAC CGG CCC ACC
```

FIG. 1A-1

```
                                            180                                         190
Val Ala Lys Val Asn Leu Gly Val Trp Val Leu Ser Leu Leu Val Ile Leu Pro Ile Val Val
GTG GCC AAG GTA AAC CTG GGC GTG TGG GTG CTA TCG CTG CTC GTC ATC CTG CCC ATC GTG GTC 200                                         210
Phe Ser Arg Thr Ala Ala Asn Ser Asp Gly Thr Val Ala Cys Asn Met Leu Met Pro Glu Pro Ala
TTC TCT CGC ACC GCG GCC AAC AGC GAC GGC ACG GTG GCT TGC AAC ATG CTC ATG CCA GAG CCC GCT 220                                         230
Gln Arg Trp Leu Val Gly Phe Val Leu Tyr Thr Phe Leu Met Gly Phe Leu Pro Val Gly Ala
CAA CGC TGG CTG GTG GGC TTC GTG TTG TAC ACA TTT CTC ATG GGC TTC CTG CCC GTG GGG GCT 240                                         250                                         260
Ile Cys Leu Cys Tyr Val Leu Ile Ile Ala Lys Met Arg Met Val Ala Leu Lys Ala Gly Trp Gln
ATC TGC CTG TGC TAC GTG CTC ATC ATT GCT AAG ATG CGC ATG GTG GCC CTC AAG GCC GGG CAG 270                                         280
Gln Arg Lys Ser Glu Arg Lys Ile Thr Leu Met Val Met Met Val Val Met Val Phe Val Ile
CAG CGC AAG TCG GAG CGC AAG ATC ACC TTA ATG GTG ATG ATG GTG GTG ATG GTG TTT GTC ATC 290                                         300
Cys Trp Met Pro Phe Tyr Val Val Gln Leu Val Asn Val Phe Ala Glu Gln Asp Asp Ala Thr Val
TGC TGG ATG CCT TTC TAC GTG GTT CAG CTG GTG AAC GTG TTT GCT GAG CAG GAC GAC GCC ACG GTG 310                                         320
Ser Gln Leu Ser Val Ile Leu Gly Tyr Ala Asn Ser Cys Ala Asn Pro Ile Leu Tyr Gly Phe Leu
AGT CAG CTG TCG GTC ATC CTC GGC TAT GCC AAC AGC TGC GCC AAC CCC ATC CTC TAT GGC TTT CTC 330                                         340
Ser Asp Asn Phe Lys Arg Ser Phe Gln Arg Ile Leu Cys Leu Ser Trp Met Asp Asn Ala Ala Glu
TCA GAC AAC TTC AAG CGC TCT TTC CAA CGC ATC CTA TGC CTC AGC TGG ATG GAC AAC GCC GCG GAG
```

FIG. 1A-2

```
                                                                    370
     350          Tyr Tyr Ala Thr Ala Leu Lys Ser Arg Ala Tyr Ser Val Glu Asp Phe Gln Pro
Glu Pro Val Asp Tyr Tyr Ala Thr Ala Leu Lys Ser Arg Ala Tyr Ser Val Glu Asp Phe Gln Pro
GAG CCG GTT GAC TAT TAC GCC ACC GCG CTC AAG AGC CGT GCC TAC AGT GTG GAA GAC TTC CAA CCT

Ser 390 391
                        380                                     Thr Thr Leu OPA
Glu Asn Leu Glu Ser Gly Gly Val Phe Arg Asn Gly Thr Cys Thr Ser Arg Ile Thr Leu OPA
GAG AAC CTG GAG TCC GGC GGC GTC TTC CGT AAT GGC ACC TGC ACG TCC CGG ATC ACG CTC TGA

GCCCGGGCCACGCAG
```

```
ACTGAAAAGCAGCC                                                                              48

1 Glu Ser Ser Gln             10 Gln Val          Val
            Met Asp Met Ala Asp Glu Leu Asn Gly Ser His Thr Trp Leu Ser
            ATG GAC ATG GCG GAT GAG CTC AAT GGA AGC CAC ACA TGG CTA TCC    108

Ser                 Leu Gly Pro Ser            Gly
    Ile Pro Phe Asp Leu Asn Gly Ser Val Val Ser Thr Asn Gln Thr Glu Pro
    ATT CCA TTT GAC CTC AAT GGC TCT GTG GTG TCA ACC AAC CAG ACA GAG CCG    168
        20

Met                                               50                Val Val
    Tyr Tyr Asp Leu Thr Ser Asn Ala Val Leu Thr Phe Ile Tyr Phe Val Val Ile Ile
    TAT GAC CTG ACA AGC AAT GCA GTC CTC ACA TTC ATC TAT TTT GTG GTC ATC ATT    228

Gly Leu Cys Gly Asn Thr Leu Val Ile Tyr Val Ile Leu Arg Tyr Ala Lys Met Lys Thr
    GGG TTG TGT GGC AAC ACA CTT GTC ATT TAT GTC ATC CTC CGC TAT GCC AAG ATG AAG ACC
        60                                      70                                      288

Ile Thr Asn Ile Tyr Ile Leu Asn Leu Ala Ile Ala Asp Glu Leu Phe Met Leu Gly Leu
    ATC ACC AAC ATT TAC ATC CTC AAC CTG GCC ATC GCA GAT GAG CTC TTC ATG CTG GGT CTG
        80                                      90                                      348

Pro Phe Leu Ala Met Gln Val Ala Leu Val His Trp Pro Phe Gly Lys Ala Ile Cys Arg
    CCT TTC TTG GCT ATG CAG GTG GCT CTG GTC CAC TGG CCC TTT GGC AAG GCC ATT TGC CGG
        100                                     110                                     408

Val Val Met Thr Val Asp Gly Ile Asn Gln Phe Thr Ser Ile Phe Cys Leu Thr Val Met
    GTG GTC ATG ACT GTG GAT GGC ATC AAT CAG TTC ACC AGC ATC TTC TGC CTG ACA GTC ATG
        120                                     130                                     468

Ser Ile Asp Arg Tyr Leu Ala Val Val His Pro Ile Lys Ser Ala Lys Trp Arg Arg Pro
    AGC ATC GAC CGA TAC CTG GCT GTC GTC CAC CCC ATC AAG TCG GCC AAG TGG AGG AGA CCC
        140                                     150
```

```
                                      160              Asn Val                    Cys      170
Arg Thr Ala Lys Met Ile Thr Met Ala Val Trp Gly Val Ser Leu Leu Val Ile Leu Pro
CGG ACG GCC AAG ATG ATC ACC ATG GCT GTG TGG GGA GTC TCT CTG CTG GTC ATC TTG CCC   528

180
Ile Met Ile Tyr Ala Gly Leu Arg Ser Asn Gln Trp Gly Arg Ser Ser Cys Thr Ile Asn
ATC ATG ATA TAT GCT GGG CTC CGG AGC AAC CAG TGG GGG AGA AGC AGC TGC ACC ATC AAC   588

200                                      Ala
Trp Pro Gly Glu Ser Gly Ala Trp Tyr Thr Gly Phe Ile Ile Ile Tyr Phe Ile Leu Gly
TGG CCA GGT GAA TCT GGT GCT TGG TAC ACA GGG TTC ATC ATC ATC TAC TTT ATT CTG GGG   648

220
Phe Leu Val Pro Leu Thr Ile Ile Cys Leu Cys Tyr Leu Arg Lys Val Thr           230
TTT CTG GTA CCC CTC ACC ATC ATC TGT CTT TGC TAC CTG CGG AAG GTG                   708

Ser Ser Gly Ile Arg Val Gly Ser Ser Lys Arg Lys Lys Ser Glu Lys Lys Val Lys
TCC TCT GGA ATC CGA GTG GGC TCC TCT AAG AGG AAG AAG TCT GAG AAG AAG GTG AAG       768

260                                      270
Met Val Ser Ile Val Val Ala Val Phe Ile Phe Cys Trp Leu Pro Phe Tyr Ile Phe Asn
ATG GTG TCC ATC GTG GTG GCT GTC TTC ATC TTC TGC TGG CTT CCC TTC TAC ATA TTC AAC   828

280      Val                             290
Val Ser Ser Val Ser Met Ala Ile Ser Pro Thr Pro Ala Leu Lys Gly Met Phe Asp Phe
GTT TCT TCC GTC TCC ATG GCC ATC AGC CCC ACC CCA GCC CTT AAA GGC ATG TTT GAC TTT   888

Ile 300                                  310
Val Val Leu Thr Tyr Ala Asn Ser Cys Ala Asn Pro Ile Leu Tyr Ala Phe Leu Ser
GTG GTG CTC ACC TAT GCT AAC AGC TGT GCC AAC CCT ATC CTA TAT GCC TTC TTG TCT       948
```

FIG. 1B-2

```
                              330
Asp Asn Phe Lys Ser Phe Gln Asn Val Leu Cys Leu Val Lys Val Ser Gly Thr Asp
GAC AAC TTC AAG AGC TTC CAG AAT GTC CTC TGC TTG AAG GTC AGC GGC ACA GAT      1008
                                                                Glu
                              350
Asp Gly Glu Arg Ser Asp Ser Lys Gln Asp Lys Ser Arg Leu Asn Glu Thr Thr Glu Thr
GAT GGG GAG CGG AGT GAC AGT AAG CAG GAC AAA TCC CGG CTG AAT GAG ACG ACC GAG ACC  1068

369
Gln Arg Thr Leu Asn Gly Asp Leu Gln Thr Ser Ile OPA
CAG AGG ACC CTC AAT GGA GAC CTC CAA ACC AGT ATC TGA ACTGCTTGGGGGGTGGGAAAGAA   1133
```

FIG. 1B-3

```
hSSTR1    1    MFPNGTASSPSSSPSSPGSCGEGGSRGPGAGAADGMEEPGRNASQNGTLSEGQGSAILISFIYSVVCLVGLCGNSMVI
               *  *     |*||  -   -   |*  -  |*  ||* |***  ****||******||**
hSSTR2    1    M:::DMADEPL::::::::NGSHTWLSIPFDLNGSVVSTNTSNQTEPYYDLTSNAVL:TFIYFVVCIIGLCGNTLVI
                                                                         M1 hSSTR1   81    YVILRYAKMKTATNIYILNLAIADELLMLSVPFLVTSTLLRHWPFGALLCRLVLSVDAVNMFTSIYCLTVLSVDRYVAVV
               ********** *||* * **** ||||| ||**|*|***
hSSTR2   66    YVILRYAKMKTITNIYILNLAIADELFMLGLPFLAMQVALVHWPFGKAICRVVMTVDGINQFTSIFCLTVMSIDRYLAVV
                                              M2                            M3 hSSTR1  161    HPIKAARYRRPTVAKVVNLGVWVLSLLVILPIVVFSRTAANSDGTVACNMLMPEPAQRWLVGFVLYTFLMGFLLPVGAIC
               ****|*||* ||  ||  **********||||    |*   *  | * |*  |||| ||  **
hSSTR2  146    HPIKSAKWRRPRTAKMITMAVWGVSLLVILPIMIYAGLRSNQWGRSSCTINWPGESGAWYTGFIIYTFILGFLVPLTIIC
                                              M4                            M5 hSSTR1  241    LCYVLIIAKMRMVALKAGWQQRKRSERKITLMVMMVVMVFVICWMPFYVVQL::::VNVFAEQDDATVSQLSVILGYANS
               *|  *|| ||| *  ||***|* * |* ||**    || |                 *|*****
hSSTR2  226    LCYLFIIIKVKSSGIRVGSSKRKKSEKKVTRMVSIVVAVFIFCWLPFYIFNVSSVSMAISPTPALKGMFDFVVVLTYANS
                                                                M6                          M7 hSSTR1  317    CANPILYGFLSDNFKRSFQRILCLSWMDNAAEEPVDYYATALKSRAYSVEDFQPENLESGGVFRNGTCTSRITTL      391
               *****|**|* -  ***  |||||  -  * *||         :::::::
hSSTR2  306    CANPILYAFLSDNFKKKSFQNVLCLVKV:SGTDDGERSDSKQDKSRLNETTETQRTLLNGD::::::::LQTSI        369
```

FIG. 2

Sequence of Human SSTR3 Gene/Protein

```
                                           1
                             Met Asp Met Leu His Pro Ser Ser Val Ser Thr Thr Ser Glu Pro Asn Ala Ser
TGACTGCTGACCACCCCTCCCCTCAGCC ATG GAC ATG CTT CAT CCA TCA TCG GTG TCC ACG ACC TCA GAA CCT AAT GCC TCC
                                                                         10
 20                                                       30                                                40
Ser Ala Trp Pro Pro Asp Ala Thr Leu Gly Asn Val Ser Ala Gly Pro Ser Pro Ala Gly Leu Ala Val Ser Gly Val
TCG GCC TGG CCC CCA GAT GCC ACC CTG GGC AAC GTG TCG GCG GGC CCA AGC CCG GCA GGG CTG GCC GTC AGT GGC GTT

Leu Ile Pro Leu Val Tyr Leu Val Val Cys Val Val Gly Leu Leu Gly Asn Ser Leu Val Ile Tyr Val Val Leu Arg
CTG ATC CCC CTG GTC TAC CTG GTG GTG TGC GTG GTG GGC CTG CTG GGT AAC TCG CTG GTC ATC TAT GTG GTG CTG CGG
 50                                                       60                                                70

His Thr Ala Ser Pro Ser Val Thr Asn Val Tyr Ile Leu Asn Leu Ala Leu Ala Asp Glu Leu Phe Met Leu Gly Leu
CAC ACG GCC AGC CCT TCA GTC ACC AAC GTC TAC ATC CTC AAC CTG GCG CTG GCC GAC GAG CTC TTC ATG CTG GGG CTG
                                       80                                                90

Pro Phe Leu Ala Ala Gln Asn Ala Leu Ser Tyr Trp Pro Phe Gly Ser Leu Met Cys Arg Leu Val Met Ala Val Asp
CCC TTC CTG GCC GCC CAG AAC GCC CTG TCC TAC TGG CCC TTC GGC TCC CTC ATG TGC CGC CTG GTC ATG GCG GTG GAT
                                                          110                                               120

Gly Ile Asn Gln Phe Thr Ser Ile Phe Cys Leu Thr Val Met Ser Val Asp Arg Tyr Leu Ala Val Val His Pro Thr
GGC ATC AAC CAG TTC ACC AGC ATA TTC TGC CTG ACT GTC ATG AGC GTG GAC CGC TAC CTG GCC GTG GTA CAT CCC ACC
                   130                                                140                                                150

Arg Ser Ala Arg Trp Arg Thr Ala Pro Val Ala Arg Thr Val Ser Ala Ala Val Trp Val Ala Ser Ala Val Val Val
CGC TCG GCC CGG TGG CGC ACA GCT CCG GTG GCC CGC ACG GTC AGC GCG GCT GTG TGG GTG GCC TCA GCC GTG GTG GTG
                   180                                                190                                                170

Leu Pro Val Val Val Phe Ser Gly Val Pro Arg Gly Met Ser Thr Cys His Met Gln Trp Pro Glu Pro Ala Ala Ala
CTG CCC GTG GTG GTC TTC TCG GGA GTG CCC CGC GGC ATG AGC ACC TGC CAC ATG CAG TGG CCC GAG CCG GCG GCG GCC
                                                                                                     200
```

FIG. 6-1

```
Trp Arg Ala Gly Phe Ile Ile Tyr Thr Ala Ala Leu Gly Phe Phe Gly Pro Leu Leu Val Ile Cys Leu Cys Tyr Leu
TGG CGA GCC GGC TTC ATC ATC TAC ACG GCC GCA CTG GGC TTC TTC GGG CCG CTG GTC ATC TGC CTC TGC TAC CTG
                        210                                              220

250
Leu Ile Val Lys Val Arg Ser Ala Gly Arg Val Trp Ala Pro Ser Cys Gln Arg Arg Arg Ser Glu Arg
CTC ATC GTG AAG GTG CGC TCA GCT GGG CGG GTG TGG GCA CCC TCG TGC CAG CGG CGC CGC TCC GAA CGC
         230                                240                                              280
                                                                                        Arg Val
                                                                                        AGG GTC

Arg Val Thr Arg Met Val Val Ala Val Val Ala Leu Phe Val Leu Cys Trp Met Pro Phe Tyr Val Leu Asn Ile Val
AGG GTC ACG CGC ATG GTG GTG GCC GTG GTG GCG CTC TTC GTG CTG TGC TGG ATG CCC TTC TAC GTG CTC AAC ATC GTC
                260                                              270
                                                        290                                    300

Asn Val Val Cys Pro Leu Pro Glu Glu Pro Ala Phe Phe Gly Leu Tyr Phe Leu Val Ala Leu Pro Tyr Ala Asn
AAC GTG TGC CCA CTG CCC GAG GAG CCT GCC TTC TTT GGG CTC TAC TTC CTG GTG GCG CTG CCC TAT GCC AAC
                                                                                        330
                310                                320

Ser Cys Ala Asn Pro Ile Leu Tyr Gly Phe Leu Ser Tyr Arg Phe Lys Gln Gly Phe Arg Arg Val Leu Leu Arg Pro
AGC TGT GCC AAC CCC ATC CTT TAT GGC TTC CTC TCC TAC CGC TTC AAG CAG GGC TTC CGC AGG GTC CTG CTG CGG CCC
                                                                                        350

Ser Arg Arg Val Arg Ser Gln Glu Glu Val Gly Pro Thr Val Gly Pro Pro Glu Lys Thr Glu Glu Glu Glu Asp
TCC CGC CGT GTG CGC AGC CAG GAG GAG GTG GGG CCC ACT GTG GGG CCC CCG GAG AAG ACT GAG GAG GAG GAG GAT
                                                        340

Gly Glu Ser Arg Glu Glu Glu Pro Gly Lys Gly Met Asn Gly Arg Val Ser Gln Ile Thr Gln Pro Gly Thr Ser
GGG GAG AGC AGG GAG GAG GAG CCC GGG AAG GGG ATG AAC GGC CGG GTC AGC CAG ATC ACG CAG CCT GGG ACC AGC
        360                                370                                              380

Gly Gln Arg Pro Pro Ser Arg Val Ala Ser Lys Glu Gln Gln Leu Leu Pro Gln Glu Ala Ser Thr Gly Glu Lys
GGG CAG CGG CCG CCC AGC AGA GTG GCC AGC AAG GAG CAG CAA CTC CTA CCC CAA GAG GCT TCC ACT GGG GAG AAG
                390                                400

418
Ser Ser Thr Met Arg Ile Ser Tyr Leu AM
TCC AGC ACG ATG CGC ATC AGC TAC CTG TAG GGGCCTGGGGAA    Translated Mol. Weight = 45854.81
410
```

FIG. 6-2

ISOLATED DNA ENCODING A SOMATOSTATIN RECEPTOR

BACKGROUND OF THE INVENTION

The National Institute of Health provided funding used in part for this invention under Grants Number DK-18347, DK-20595 and DK-42086. Accordingly, the federal government may have certain rights in this invention pursuant to 35 U.S.C. §202.

1. Field of the Invention

This invention relates generally to compositions of and methods for obtaining somatostatin receptors (SSTRs). The invention relates as well to the DNA sequences encoding somatostatin receptors, the recombinant vectors carrying those sequences, the recombinant host cells including either the sequences or vectors, and recombinant somatostatin receptor polypeptides. In particular embodiments, the invention relates to the cloning and functional expression of at least three different somatostatin receptors, SSTR1, SSTR2 and SSTR3 from a variety of sources including human DNA. The invention includes as well, methods for using the isolated, recombinant receptor polypeptides in assays designed to select and improve among candidate substances such as agonists and antagonists of somatostatin receptor polypeptides for use in diagnostic, drug design and therapeutic applications.

2. Description of the Related Art

SOMATOSTATIN

Somatostatin is a tetradecapeptide that was first isolated from hypothalamic extracts and shown to be a potent inhibitor of growth hormone secretion from the anterior pituitary (Brazeau et al. 1973). Subsequent studies have shown that this hormone is widely distributed, occurring in the central nervous system and peripheral tissues of the body such as the stomach, the intestines, and pancreas (Reichlin 1983). It is known that somatostatin has diverse physiological effects that are tissue specific (Reichlin 1983). It can, for instance, function as a neurotransmitter as well as a hormone. Its hormonal effects include suppression of the release of many pituitary, pancreatic and gastrointestinal hormones and other secretory proteins. For these reasons, treatment of patients with native somatostatin may have numerous, and undesirable effects. A much preferred mode of treatment would allow segregating the desired therapeutic effect from undesirable physiological effects. At present, the only way to perfect such drugs is through the use of whole animal studies or by using crude isolations of these receptors.

Somatostatin is a member of a family of somatostatin-like peptides (Pradayrol et al. 1980; Esch et al. 1980). The two principle bioactive forms of somatostatin, somatostatin-14 and somatostatin-28, are derived via a tissue-specific proteolytic processing of prosomatostatin, a 92 amino acid precursor (Shen et al. 1982). It is known, as well, that somatostatin-14 and somatostatin-28 may be found in varying concentrations in different tissues.

Although somatostatin-14 and somatostatin-28 may have common effects on target tissues, they show different potencies suggesting that their actions are mediated by different receptors (Reichlin 1983). For example, somatostatin-14 appears to be relatively more selective for inhibition of glucagon and gastric acid secretion, whereas somatostatin-28 is a more specific inhibitor of growth hormone, insulin and pancreatic exocrine secretion (Wass 1989).

SOMATOSTATIN RECEPTORS

Somatostatin-14 and somatostatin-28 exert their biological effects by binding to high affinity receptors that appear in many cases to be coupled to GTP-binding (G) proteins (Reisine et al. 1985; Lewis et al. 1985). Pharmacological studies indicate that there are at least two sub-types of somatostatin receptor (Srikant and Patel 1981; Tran et al. 1985). It is presumed that the two sub-types of somatostatin receptor reflect receptors that are selective for either somatostatin-14 or somatostatin-28. It is assumed that somatostatin receptors will be similar to other transmembrane signaling receptors.

Many such transmembrane signaling systems consist of at least three membrane-bound protein components: (a) a cell-surface receptor; (b) an effector, such as an ion channel or the enzyme adenylyl cyclase; and (c) a guanine nucleotide-binding regulatory protein or G protein, that is coupled to both the receptor and its effector.

G protein-coupled receptors mediate the actions of extracellular signals as diverse as light, odorants, peptide hormones and neurotransmitters. Such receptors have been identified in organisms as evolutionarily divergent as yeasts and man. Nearly all G protein-coupled receptors bear sequence similarities with one another, and it is thought that all share a similar topological motif consisting of seven hydrophobic (and potentially α-helical) segments that span the lipid bilayer (Dohlman et al. 1987; Dohlman et al. 1991).

All seven-transmembrane segment receptor-coupled G proteins consist of three tightly associated subunits, α, β and γ (1:1:1) in order of decreasing mass. Following agonist binding to the receptor, a conformational change is transmitted to the G protein, which cause the α-subunit to exchange a bound GDP for GTP and to dissociate from the βγ-subunits. The GTP-bound form of the α-subunit is typically the effector-modulating moiety. Signal amplification results from the ability of a single receptor to activate many G protein molecules, and from the stimulation by Gα-GTP of several catalytic cycles of the effector.

The family of regulatory G proteins comprises a multiplicity of different α-subunits (greater than twenty in man), which associate with a smaller pool of β- and γ-subunits (greater than four each) (Strothman and Simon 1991). Thus, it is anticipated that differences in the α-subunits probably distinguish the various G protein oligomers, although the targeting or function of the various α-subunits might also depend on the βγ subunits with which they associate (Strothman and Simon 1991).

Certain somatostatin receptors have been at least partially purified (Patel et al. 1990). In these studies, analogs of the natural occurring ligands of somatostatin receptors (i.e. somatostatin or somatostatin analogs) were used to cross-link to membrane somatostatin receptors in rat brain, pituitary, exocrine pancreas, and adrenal cortex using a number of chemical and photoaffinity cross-linkers. Two major somatostatin receptor proteins of 58-kDa and 27-kDa were identified. These proteins exhibited a tissue-specific distribution: the 58-kDa protein was the dominant form (approximately 90% of total labeled protein) in the pituitary, adrenal, and exocrine pancreas, whereas the 27-kDa moiety was the principle somatostatin receptor in brain (approximately 80% of total labeled protein). Two minor, specifically-labeled somatostatin receptor proteins of 32-kDa and 42-kDa were found, respectively, in the brain and pancreas only.

Using the same two ligands, these workers characterized the somatostatin receptor from cell lines which show a relative preference for binding somatostatin-28 and somatostatin-14. Three specific somatostatin receptor proteins of 58-kDa, 42-kDa and 27-kDa were identified in one such cell line (AtT-20 cells). By contrast, in GH$_3$ cells, the 27-kDa protein and not the 58-kDa species was the dominant component. Labeling of each of these major and minor proteins was sensitive to inhibition by GTP and somatostatin-14, attesting to their specificity as putative somatostatin receptor proteins.

Recently, He et al. have purified a detergent solubilized 60 kDa somatostatin receptor protein from rat brain and AtT-20 cells on a D-Trp$^8$SS-14 affinity column (He et al. 1989). The size of this protein agrees closely with that of Patel et al. who were able to cross-link and purify a 58-kDa receptor also from rat brain and AtT-20 cells. Thus, a comparably sized protein of 58 to 60-kDa, which binds somatostatin-14 and somatostatin-28 with high affinity and specificity thereby qualifying as a pharmacologic receptor, has been purified by two different approaches from two different tissues, and by two different groups of researchers. Furthermore, the size is consistent with that of other cloned G-protein-linked membrane receptors.

A different size somatostatin receptor protein of 90-kDa has been purified to homogeneity by Reyl-Desmars et al. from a human gastric cell line HGT1 using an anti-receptor monoclonal antibody (Reyl-Desmars et al. 1989). Attempts to sequence the intact 58kDa protein purified from the AtT-20 cells at first met failure due to a blocked-N-terminus. Accordingly, these workers proceeded to trypsinize the brain 58-kDa protein. The digest was analyzed by high performance liquid chromatography. A number of peptide peaks were identified which were not present in a control digest. The largest four of these peaks containing 20 to 40 picomoles of protein were each sequenced. Four hitherto unknown peptide sequences of 16 to 23 amino acid residues were obtained. The largest of these fragments showed partial sequence homology with the G$_i$ protein family. However, the sequence did not correspond to any known G protein, nor did the sequence of the remaining tryptic fragment show any resemblance to a G protein.

It is, thus, conceivable that the partial sequence homology of one of the tryptic fragments to G$_i$ is coincidental or alternatively, it may signify a G protein-related structure of the 58-kDa somatostatin receptor, comparable perhaps to that of other recently characterized GTP-binding receptors such as the signal recognition particle receptor (Connolly and Gilmore 1989). The 32-kDa protein also isolated by Patel et al. has proved to resist sequence analysis (Dohlman, 1991).

CLONING OF SEVEN-TRANSMEMBRANE SEGMENT RECEPTORS

Improvements in cell culture and in pharmacological methods, and more recently, use of molecular cloning and gene expression techniques have led to the identification and characterization of many new seven-transmembrane segment receptors, including new sub-types and sub-sub-types of previously identified receptors. The $\alpha_1$ and $\alpha_2$-adrenergic receptors once thought to each consist of single receptor species, are now known to each be encoded by at least three distinct genes (Kobilka et al. 1987; Regan et al. 1988; Cotecchia et al. 1988; Lomasney 1990). In addition to rhodopsin in rod cells, which mediates vision in dim light, three highly similar cone pigments mediating color vision have been cloned (Nathans et al. 1986a; and Nathans et al. 1986b). All of the family of G protein-coupled receptors appear to be homologous with other members of the family of G protein-coupled receptors (e.g., dopaminergic, muscarinic, serotonergic, tachykinin, etc.), and each appears to share the characteristic seven-transmembrane segment topography.

When comparing the seven-transmembrane segment receptors with one another, a discernible pattern of amino acid sequence conservation is observed. Transmembrane domains are often the most similar, whereas the N-C terminal regions and the cytoplasmic loop connecting transmembrane segments V and VI can be quite divergent (Dohlman et al. 1987).

Interaction with cytoplasmic proteins, such as kinases and G proteins, was predicted to involve the hydrophobic loops connecting the transmembrane domains of the receptor. The challenge, however, has been to determine which features are preserved among the seven-transmembrane segment receptors because of conservation of function, and which divergent features represent structural adaptations to new functions. A number of strategies have been used to test these ideas, including the use of recombinant DNA and gene expression techniques for the construction of substitution and deletion mutants, as well as of hybrid or chimeric receptors (Dohlman et al. 1991).

With the growing number of receptor sub-types, G proteins, and effectors, characterization of ligand binding and G protein recognition properties of these receptors is an important area for investigation. It has long been known that multiple receptors can couple to a single G protein and, as in the case of epinephrine binding to $\beta_2$- and $\alpha_2$-adrenergic receptors, a single ligand can bind to multiple functional distinct receptor sub-types. Moreover, G proteins with similar receptors and effector coupling specificities have also been identified. For example, three species of human G$_i$ have been cloned (Itoh et al. 1988), and alternate mRNA splicing has been shown to result in multiple variants of G$_s$ (Kozasa et al. 1988). Cloning and over production of the muscarinic and $\alpha_2$-adrenergic receptors led to the demonstration that a single receptor sub-type, when expressed at high levels in the cell, will couple to more than one type of G protein.

Given this complexity and apparent degeneracy of function, a question of fundamental importance is how, and under what circumstances, can G proteins organize signals from multiple receptors and direct them to the appropriate effectors. A traditional approach has been to reconstitute the purified receptor and G protein components in vitro. Unfortunately, purification schemes have been successful for only a very limited number of receptor sub-types and their cognate G-proteins. Alternatively, heterologous expression systems may be of more general usefulness in the characterization of cloned receptors and in elucidating receptor G protein coupling specificity (Marullo et al. 1988; Payette et al. 1990; King et al. 1990). Studies of this type are necessary in order to successfully design therapeutic approaches in diseases related to somatostatin.

Once such system was recently developed in yeast cells, in which the genes for a mammalian $\beta_2$-adrenergic receptor and G$_s$ $\alpha$-sub-unit were coexpressed (King et al. 1990). Expression of the $\beta_2$-adrenergic receptor to levels several hundred-fold higher than any human tissue was attained, and ligand binding was shown to be of the appropriate affinity, specificity, and stereoselectivity. Moreover, a $\beta_2$-adrenergic receptor-mediated activation of the pheromone signal transduction pathway was demonstrated by several criteria, including imposition of growth arrest, morphological changes, and induction of a pheromone-responsive promoter (FUS1) fused to the *Escherichia coli* lacz gene (encoding $\beta$-galactosidase) (King et al. 1990).

Finally, expression of a single receptor in the absence of other related sub-types is often impossible to achieve, even in isolated, non-recombinant mammalian cells. Thus, expression in a microorganism where no such endogenous receptors exist (e.g. yeast cells or mutant mammalian cell lines) can be useful for screening and evaluating sub-type-selective drugs (Marullo et al. 1988; Payette et al. 1990; and King et al. 1990).

Thus, it has been considerably difficult to apply the standard approaches of classical genetics or even the powerful techniques of molecular biology to the study of somatostatin receptors. In particular means are needed for the identification of the DNA sequences encoding individual somatostatin receptors. Given such isolated, recombinant sequences, it may be possible to address the heretofore intractable problems associated with design and testing of isoform-specific somatostatin receptor agonists and antagonists.

SUMMARY OF THE INVENTION

The present invention for the first time, provides DNA segments, purified polypeptides, methods for obtaining antibodies, methods of cloning and using recombinant host cells, necessary to obtain and use recombinant somatostatin receptors. Thus, the difficulties encountered with applying the standard approaches of classical genetics or techniques in molecular biology evident in the prior art, such as the diversity of molecular weight sizes as ascribed to somatostatin receptors, have been overcome. Accordingly, the present invention concerns generally compositions and methods for the preparation of somatostatin receptors including those of both human and mouse origin.

In order to achieve the substantial advantages of the present invention, a variety of novel compositions of matter and methods are provided. The compositions of matter provided by the present invention include recombinant vectors incorporating DNA encoding somatostatin receptor polypeptides, isolated DNA segments encoding somatostatin receptors, somatostatin receptor polypeptides themselves, and recombinant host cells incorporating DNA encoding somatostatin receptor polypeptides. The methods of the present invention include methods for producing somatostatin receptor polypeptides and antibodies thereto, screening assays for testing candidate substances including agonists and antagonists of somatostatin receptor polypeptides, such assays capable of discriminating candidate substances with desirable versus undesirable properties, such assays capable of selecting amongst candidate substances specific to one or another of the somatostatin receptor polypeptides, and methods of investigating structure function relationships of the somatostatin receptor polypeptides.

In the context of the present invention, the term somatostatin receptor polypeptide is intended to refer to peptides or proteins having the biological and the immunological identity of the somatostatin receptor polypeptides enabled by the present invention. For example, such receptor polypeptides include those derived from the human and mouse sources identified in the present invention. Generally, the somatostatin receptor polypeptide of the invention will refer to any of the amino acid sequences presented in the present application since these are the precise length and precise nature of the only presently sequenced and known somatostatin receptor polypeptides. However, the invention does not preclude and, in fact, enables preparation or use of shorter or longer peptides, polypeptides or proteins, so long as a peptide or a protein has a similar in kind biological activity and/or a cross-reactive immunological reactivity, for example, as defined by a polyclonal antisera directed against any of the somatostatin receptor polypeptides identified herein. For instance, it will be understood by those of skill in the art that different eukaryotic sources including other mammalian sources as well as different tissue sources within a given species are likely to provide recombinant somatostatin receptor polypeptides by using the methods of the invention.

DNA SEGMENTS

Recombinant vectors as disclosed herein will, using the methods and compositions of the present invention, include a DNA segment having a sequence encoding a somatostatin receptor polypeptide. Such a DNA segment is meant to include a segment of DNA encoding a somatostatin receptor polypeptide sufficient in length to distinguish said segment from a DNA segment encoding a non-somatostatin receptor polypeptide. The somatostatin receptor polypeptide of the present invention will be understood to be any somatostatin receptor polypeptide capable of binding somatostatin in any of its forms or analogs of somatostatin. In addition, the somatostatin receptor polypeptide of the invention is not limited to a particular source. As disclosed herein, the techniques and compositions of the present invention provide, for example, the identification and isolation of SSTRs 1–3 from both human and mouse sources. Thus, the invention provides for the general detection and isolation of the genus of somatostatin receptor polypeptides from a variety of sources while identifying specifically three species of that genus from two separate sources. It is believed that a number of species of the family of somatostatin receptor polypeptides will be amenable to detection and isolation using the compositions and methods of the present inventions. At present, it is believed that at least four members of this family of receptor polypeptides is accessible using the compositions and methods of the present invention. The DNA segments of the invention may also encode biologically functional proteins or peptides which have variant amino acid sequences, such as with changes selected based on considerations such as the relative hydropathic score of the amino acids being exchanged. These variant sequences may be those isolated from natural sources or may be those induced in the sequences disclosed herein using a mutagenic procedure such as site-directed mutagenesis.

In certain general aspects, the invention relates to preparation and use of DNA segments, including vectors or DNA fragments, having a sequence encoding a somatostatin receptor polypeptide. The DNA segments of the invention can, of course, be used for the expression of the somatostatin receptor polypeptides of the invention.

In certain embodiments, the vector will contain a substantially purified DNA fragment which encodes at least a useful portion of a somatostatin receptor polypeptide which includes the amino acids depicted in any one of the sequence ID numbers showing the sequence of a somatostatin receptor polypeptide. In the case of somatostatin receptor polypeptides for SSTR1, both a human (sequence ID No. 2) and mouse (sequence ID No. 4) polypeptide are enabled by the present invention. Likewise, a human SSTR2 and a mouse SSTR2 are enabled by the present invention and are depicted in sequence ID Nos. 6 and 8, respectively. Additionally, a human SSTR3 polypeptide is depicted in sequence ID No. 10, while a mouse SSTR3 polypeptide is depicted in sequence ID No. 12.

In certain embodiments of the invention, it is contemplated that DNA fragments, both shorter and longer, which incorporate sequences from any of the variety of any of the sequence ID numbers depicting DNA encoding somatostatin receptor polypeptides, will find additional utility, including uses as short DNA fragment hybridization probes, e.g., in screening both prokaryotic and eukaryotic recombinant clone banks. In any event, fragments corresponding to the sequences in any of the sequence ID Nos. showing DNA sequences encoding somatostatin receptor polypeptides, for stretches as short as 14 or so nucleotides, will generally find utility in accordance with these or other embodiments. By having stretches of at least about 14 nucleotides in common with the somatostatin receptor DNA sequence of any of the sequence ID listing for SSTRs 1 through 3, or any of their complements, a DNA segment will typically have the ability to form a preferential hybridization with somatostatin receptor species DNA, particularly under more stringent conditions such as 0.15M sodium chloride and 0.02M sodium citrate, pH 7.4 at about 50° C.

While such a complementary or common stretch will typically ensure the ability to form a stable hybrid, longer stretches of complementary DNA may prove more desirable for certain embodiments. Thus, one may desire to use DNA segments incorporating longer stretches of complementarily, for example, on the order of 20, 30, or even 40 or so bases. Of course, the longer the complementary sequences used, the greater the degree of hybridization possible and the more stringent can be the hybridization protocols.

Thus, the DNA sequences of the present invention may be used for hybridizing as oligonucleotide probes to a DNA source suspected of possessing a somatostatin receptor polypeptide or gene. The probing will usually be accomplished by hybridizing the oligonucleotide to a DNA source suspected of possessing such a receptor gene. In some cases, the probes will constitute only a single probe, and in others, the probes will constitute a collection of probes based on a certain amino acid sequence or sequences of the somatostatin receptor polypeptide and will account in their diversity for the redundancy inherent in the genetic code.

A suitable source of DNA for probing in this manner will be capable of expressing somatostatin receptor polypeptides and may be a genomic library of a cell line of interest (e.g., human pancreatic islets cells. Alternatively, a source of DNA may include total DNA from the cell line of interest. Once the hybridization process of the invention has identified a candidate DNA segment, one will desire to confirm that a positive clone has been obtained, e.g., by further hybridization, sequencing and/or expression and testing.

Alternatively, these segments may be used in a number of techniques including their use as: (1) diagnostic tools to detect normal and abnormal DNA sequences in DNA derived from patient's cells; (2) means for detecting and isolating other members of the somatostatin receptor family and related proteins from a DNA library potentially containing such sequences; (3) primers for hybridizing to related sequences for the purpose of amplifying those sequences; (4) primers for altering the native somatostatin receptor DNA sequences; as well as other techniques which rely on the similarity of the DNA sequences to those of the somatostatin receptor DNA segments herein disclosed.

VECTORS

The present invention provides, in one aspect, for a recombinant vector incorporating a DNA segment having a sequence encoding a somatostatin receptor polypeptide. Such a vector may be any of those vectors known well to those of skill in the art capable of incorporating an appropriate DNA segment encoding a somatostatin receptor polypeptide and capable of stable transformation in a host cell. Such a vector includes the mammalian expression vectors of the pCMV family including pCMV6b and pCMV6c (Chiron Corp., Emeryville Calif.). In certain cases, and specifically in the case of these individual mammalian expression vectors, the resulting constructs may require co-transfection with a vector containing a selectable marker such as pSV2neo. Via co-transfection into a dihydrofolate reductase-deficient Chinese hamster ovary cell line, such as DG44, clones expressing somatostatin polypeptides by virtue of DNA incorporated into such expression vectors may be detected.

The invention provides, in one aspect, vectors incorporating DNA segments having sequences encoding somatostatin receptor polypeptides where the sequence encodes a polypeptide which includes the amino acids numbered 1 to 391 of either of the sequences shown in sequence ID No. 2 or 4, which sequences correspond to the amino acid sequences for the human and mouse SSTR1 polypeptide, respectively. The recombinant vector may also incorporate a DNA segment having a sequence encoding of somatostatin receptor polypeptide which polypeptide includes amino acids 1 to 369 of either of the sequences depicted in sequence ID Nos. 6 or 8, which sequences correspond to the amino acid sequences for the human and mouse SSTR2 polypeptide, respectively. Additionally, the recombinant vector may incorporate a DNA segment encoding, in its sequence, a somatostatin receptor polypeptide which polypeptide includes the amino acids 1 to 418 of the sequence ID No. 10, or which polypeptide includes the amino acids 1 to 428 of the sequence ID number 12, and which sequences correspond to the SSTR3 polypeptide of human and mouse, respectively. Additionally, it will be understood, by those of skill in the art, that additional somatostatin receptor polypeptides, the identification, cloning and sequencing of which are enabled by the present application, may also be incorporated into a vector and will be, therefore, covered by the present invention.

For vectors, any number are known in which DNA sequences of the invention may be incorporated. For instance, the vector pUC18 has been demonstrated to be of particular value. Likewise, the related vectors M13mp18 and M13mp19 may be used in certain embodiments of the invention, in particular, in performing dideoxy sequencing.

Recombinant vectors and isolated segments may, therefore, variously include the basic somatostatin receptor polypeptide coding region itself of any of the somatostatin receptor polypeptides noted above or it may contain coding regions bearing selected alterations or modifications in the basic coding region of such a somatostatin receptor polypeptide. Alternatively, such vectors or fragments may code larger proteins or polypeptides which nevertheless include the basic coding region. In any event, it should be appreciated that due to codon redundancy as well as biological functional equivalence, this aspect of the invention is not limited to the particular DNA sequences corresponding to the polypeptide sequences noted above.

Recombinant vectors such as those described above are useful both as a means for preparing quantities of the somatostatin receptor polypeptide-encoding DNA itself, and as a means for preparing the encoded protein and peptides. It is contemplated that where somatostatin receptor proteins of the invention are made by recombinant means, one may employ either prokaryotic or eukaryotic expression as shuttle systems. However, in that prokaryotic systems are usually incapable of correctly processing precursor proteins and, in particular, such systems are incapable of correctly processing membrane associated eukaryotic proteins, and since eukaryotic somatostatin receptor polypeptides are anticipated using the teaching of the disclosed invention, one may desire to express such sequences in eukaryotic hosts. However, even where the DNA segment encodes a eukaryotic somatostatin receptor polypeptide, it is contemplated that prokaryotic expression will have some additional applicability. Therefore, the invention can be used in combination with vectors which can shuttle between the eukaryotic and prokaryotic cells. Such a system is described herein which allows the use of bacterial host cells as well as eukaryotic host cells.

Where expression of recombinant somatostatin receptor polypeptides are desired and a eukaryotic host is contemplated, it most likely will be desirable to employ a vector such as a plasmid, that incorporates a eukaryotic origin of replication. Additionally, for the purposes of expression in eukaryotic systems, one will desire to position the somatostatin receptor encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the protein between about 1 and about 50 nucleotides 3' of or downstream with respect to the promoter chosen. Furthermore, where eukaryotic expression is anticipated, one would typically desire to incorporate into the transcriptional unit which includes the somatostatin receptor polypeptide, an appropriate polyadenylation side. Typically, the polyadenylation side is about 30 to 2,000 nucleotides downstream of the termination site of the protein at a position prior to the transcription termination side.

Accordingly, in certain preferred embodiments, the vectors of the invention are those where the somatostatin receptor polypeptide encoding sequence is positioned adjacent to and under the control of an effective promoter. The vectors may be that set of vectors known well to those of skill in the art where the promoter comprises a prokaryotic promoter, the vector being adapted for expression in a prokaryotic host cells. Alternatively, the vectors may be those of common knowledge to skilled artisans where the promoter comprises a eukaryotic promoter and the vector further includes a polyadenylation signal positioned 3' of the carboxy-terminal amino acid, and within a transcriptional unit of the encoded protein.

HOST CELLS

The invention also provides a means for obtaining a variety of recombinant host cells which incorporated DNA sequence in accordance with those depicted in sequence ID Nos. 1, 3, 5, 7, 9 or 11. The host cell may be prokaryotic or eukaryotic in nature. In any case, it is understood that the DNA segment encoding a somatostatin receptor polypeptide will also possess the regulatory signals functional in a particular host cell.

A preferred embodiment includes a recombinant eukaryotic cell. Where it is of interest to produce a human somatostatin receptor polypeptide, those eukaryotic cell lines derived from human tissue will be of particular interest.

ISOLATING SOMATOSTATIN RECEPTOR GENES AND POLYPEPTIDES

The invention also provides methods for isolating somatostatin receptor polypeptides from both recombinant and nonrecombinant sources. Such a protein will typically include an amino acid sequence corresponding to amino acids 1 to 391 of either of sequence ID Nos. 2 or 4, or an amino acid sequence corresponding to amino acids 1 to 369 of either of sequence ID No. 6 or 8.

However, the methods of the invention have been demonstrated to be successful in isolating a somatostatin receptor polypeptide from human pancreatic islet cells which polypeptide includes at least the amino acids 1 to 418 of sequence ID No. 10. Likewise, the techniques of the present invention have been used to isolate a somatostatin receptor polypeptide from mouse DNA which polypeptide includes at least the amino acids 1 to 428 of sequence ID No. 12. It will be obvious to those of skill in the art that these somatostatin receptor polypeptides correspond to polypeptides different in amino acid sequence from either somatostatin receptors 1 or 2 as described extensively herein. It will likewise to one of skill in the art and as particularly pointed out in the background to the present invention, that there are a variety of somatostatin receptors that have been at least partially purified. As noted previously, at least two major somatostatin receptor proteins of 58-kDa and 27-kDa have been identified. In addition, specifically labeled somatostatin receptor proteins of 32-kDa and 42-kDa have been localized as well. A 90-kDa somatostatin receptor protein has been purified to a homogeneity from a human gastric cell line as noted previously, as well.

Thus, different molecular weight polypeptides possessing somatostatin receptor activity are anticipated by the present invention. Further, the differences in molecular weight for the various somatostatin receptors enabled by the present application may be related to possible differential glycosylation, or such differentials may represent totally different somatostatin receptor forms, perhaps unique to humans, or to gut tissues, or to specific tissues. Thus, it will be obvious to skilled artisans that the differences in molecular weights of the various somatostatin receptor polypeptides described in the prior art are predicted to have somatostatin receptor activity and yet may have substantially similar DNA or amino acid sequences. Thus the different activity may result from actual differences in the primary structure of the amino acid chains themselves or may result from any number of post-translation modifications. However, where such a protein represents a sequence enabled herein regardless of such post-translation or modifications which may give rise to differential molecular weights, it will be understood by skilled artisans to be enabled by the present invention. It would be understood by those of skill in the art that such a protein when encoded in a recombinant DNA molecule may be used to directly synthesize a somatostatin receptor polypeptide when provided the proper host cell and genetic approach.

Additionally, such polypeptides may be used in a method for the preparation of an antibody for use in certain embodiments. Such antibodies may be either a polyclonal or monoclonal antibody which, in any case, represents an antibody immunologically reactive with any of the polypeptides of the invention. Once such an antibody is produced, this antibody may in turn be used in combination with expression libraries to screen for additional members of the somatostatin receptor-like family of polypeptides.

EXPRESSING SOMATOSTATIN POLYPEPTIDES

The invention provides, therefore, a method of producing a recombinant somatostatin receptor polypeptide. This method includes the use of a recombinant host cell where the recombinant host cell is capable of expressing a recombinant somatostatin receptor polypeptide. Furthermore, the method for producing recombinant somatostatin receptor polypeptides provided in the invention includes culturing the host cell under conditions appropriate for the expression of the polypeptide. Finally, the method of production claimed includes collecting the polypeptide thus expressed.

The method is particularly applicable where one desires to obtain a polypeptide corresponding to any of the polypeptides identified in sequence IDs No. 2, 4, 6, 8, 10 or 12. However, the method may be directed to isolation of a somatostatin receptor polypeptide and a gene that is encoding such a polypeptide that is substantially similar to any of the polypeptides described above. In particular embodiments, the method would typically involve selecting cells that are capable of expressing a somatostatin receptor polypeptide, in particular in Chinese hamster ovary cells. However, a variety of cells are amenable to the methods of the invention, for instance, cells of yeasts, human cell lines, and other eukaryotic cell lines known well to those of the art. Of course, methods would typically involve culturing such cells such that the somatostatin receptor polypeptide is produced in substantial quantity.

In certain general aspects, then, a method of producing a recombinant somatostatin receptor polypeptide is provided by the invention. First, one produces a recombinant host cell according to the methods and with the compositions of the invention such that the recombinant cells so produced is capable of expressing the polypeptide. Next, one cultures the host cell under conditions appropriate for expressing the polypeptide. Finally, according to the methods and with the compositions of the invention the recombinant polypeptide is recovered.

ASSAYS USING RECOMBINANT SOMATOSTATIN RECEPTOR

The recombinant somatostatin receptor polypeptide expressed by these methods may be used as in a variety of screening assays. For instance, utilizing the methods and compositions of the present invention, screening assays for the testing of candidate substances such as agonists and antagonists of somatostatin receptors may be derived. A candidate substance is a substance which potentially may interact with or modulate, by binding or other intramolecular interaction, a somatostatin receptor polypeptide. In some instances, such a candidate substance will be an agonist of the receptor and in other instances may exhibit antagonistic attributes when interacting with the receptor polypeptide. In other instances, such substances may have mixed agonistic and antagonistic properties or may modulate the somatostatin receptor in other ways.

Screening assays of the present invention will generally involve determining the ability of a candidate substance to affect the activity of the receptor, such as the screening of candidate substances to identify those that will inhibit or otherwise modify the receptor's function. Typically, this method will include recombinantly preparing receptor polypeptide, followed by testing the recombinant polypeptide with a candidate substance to determine the ability of the substance to affect its enzymatic function. In preferred embodiments, the invention relates to the screening of candidate substances to identify those that affect the enzymatic activity of the human receptor, and thus may be suitable for use in humans.

In a typical screening assay for identifying candidate substances, one may desire to employ the same recombinant expression host as the starting source for obtaining the receptor polypeptide, generally prepared in the form of a crude homogenate. Recombinant cells expressing the receptor may be washed and homogenized to prepare a crude protein homogenate in a desirable buffer such as disclosed herein. In a typical assay, an amount of protein from the cell homogenate, is placed into a small volume of an appropriate assay buffer at an appropriate pH. Candidate substances, such as agonists and antagonists, are added to the admixture in convenient concentrations and the interaction between the candidate substance and the receptor polypeptide is monitored.

Where one uses an appropriate known substrate for the receptor, one can, in the foregoing manner, obtain a baseline activity for the recombinantly produced receptor. Then, to test for inhibitors or modifiers of the receptor function, one can incorporate into the admixture a candidate substance whose effect on the receptor is to be tested. By comparing reactions which are carried out in the presence or absence of the candidate substance, one can then obtain information regarding the effect of the candidate substance on the normal function of the receptor.

Accordingly, it is proposed that this aspect of the present invention will provide those of skill in the art with methodology that will allow for the identification of candidate substances having the ability to modify the action of somatostatin receptor polypeptides in one or more manners.

In one embodiment, such an assay may be designed to be capable of discriminating those candidate substances with the desirable properties of somatostatin but which lack the undesirable properties of somatostatin such as the inhibition of insulin or glucagon release and vice versa. In another embodiment, screening assays for testing candidate substances such as agonists and antagonists of somatostatin receptors may be used to identify such candidate substances having selective ability to interact with one or more of the somatostatin receptor polypeptides but which polypeptides are without a substantially overlapping activity with another of the somatostatin receptor polypeptides identified herein.

Additionally, screening assays for the testing of candidate substances may be designed to allow the investigation of structure activity relationships of somatostatin with the receptors, e.g., study of binding of naturally occurring hormones or other substances capable of interacting or otherwise modulating with the receptor versus studies of the activity caused by the binding of such molecules to the receptor. In certain embodiments, the polypeptides of the invention may be crystallized in order to carry out x-ray crystallographic studies as a means of evaluating interactions with candidate substances or other molecules with the somatostatin receptor polypeptide. For instance, with the purified recombinant polypeptides of the invention, when crystallized in a suitable form, will be amenable to detection of intra-molecular interactions by x-ray crystallography.

BRIEF DESCRIPTION OF THE DRAWINGS

FIGS. 1A and 1B. Primary structure of two somatostatin receptors. Nucleotide and predicted amino acid sequences of the human SSTR1 (A) and SSTR2 (B) genomic clones. The number of the nucleotide relative to the translation start site is indicated at the end of each line. Amino acid residues of the corresponding mouse proteins that differ from those of the human somatostatin receptors are shown above the human sequences.

FIG. 2. Comparison of the amino acid sequences of human SSTR1 and 2. Amino acids are indicated by their single-letter abbreviations. Asterisks denote identical amino acids and bars indicate chemically similar residues. Gaps introduced to generate this alignment are represented by colons. The seven predicted transmembrane domains (M1–M7) are noted. The amino acid residues that are conserved within the superfamily of G protein-coupled receptors are shown in bold type.

FIG. 6. Sequence of human SSTR3.

DESCRIPTION OF PREFERRED EMBODIMENTS

Figure 3A:
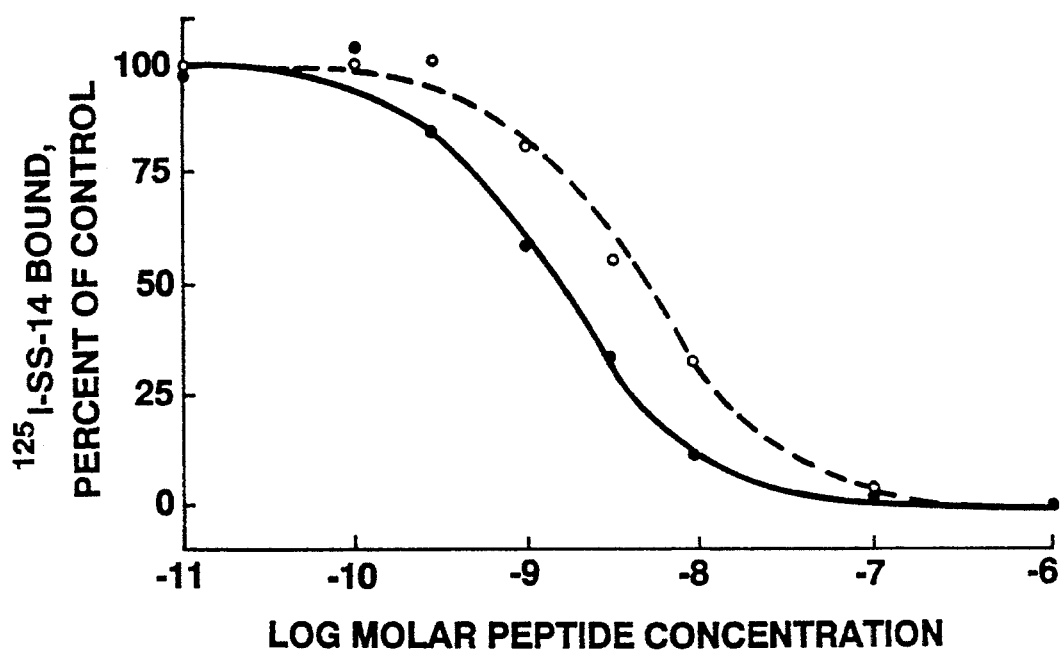
FIGS. 3A and 3B. Binding of [[$I^{125}$]iodo-Tyr$^{11}$]-somatostatin-14 to CHO cells expressing SSTR1 and SSTR2. A, cells transfected with human SSTR1; B, cells transfected with mouse SSTR2. Data (the mean of duplicate determinations) have been normalized to account for radiolabeled ligand bound in the absence of inhibitor (control binding, 1425 cpm for panel A and 2080 cpm for panel B), and have been corrected for non-specific binding (radiolabeled ligand bound in the presence of 1 µM somatostatin-14, 225 cpm in both cases). Inhibition of binding in the presence of 1 µM somatostatin-14, respectively. Curves have been modeled in terms of ligand interaction with a single population of binding sites.

As will be described in detail below, the compositions of matter and methods of the present invention are generally applicable to somatostatin receptors regardless of the source or the precise sequence of the receptor molecule. Therefore, there are a number of generally applicable techniques which may be used and which are described below. Additionally, examples are provided illustrating the applicability of the general techniques to several specific somatostatin receptor polypeptides from both human and mouse sources.

Host Cell Cultures and Vectors

In general, of course, prokaryotes are preferred for the initial cloning of DNA sequences and constructing the vectors useful in the invention. For example, E. coli K12 strains may be particularly useful. Other microbial strains which may be used include E. coli B, and E. coli X1776 (ATCC No. 31537). These examples are, of course, intended to be illustrative rather than limiting.

Prokaryotes may also be used for expression. The aforementioned strains, as well as E. coli W3110 (F-, lambda-, prototrophic, ATCC No. 273325), bacilli such as Bacillus subtilus, or other enterobacteriacea such as Salmonella typhimurium or Serratus marcesans, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

Those promoters most commonly used in recombinant DNA construction include the β-lactamase (penicillinase) and lactose promoter systems (Chang et al., 1978; Itakura et al., 1977; Goeddel et al., 1979; Goeddel et al., 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to ligate them functionally with plasmid vectors (Siebwenlist et al., 1980).

In addition to prokaryotes, eukaryotic microbes, such as yeast cultures may also be used. Saccharomyces cerevisiase or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequences desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propogation of vertebrate cells in culture (tissue culture) has become a routine procedure in recent years (Kruse and Peterson, 1973). Examples of such useful host cell lines are AtT-20, VERO and HeLa cells, Chinese hamster ovary (CHO) cell lines, and W138, BHK, COSM6, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin or replication. Further, it is also possible, and often desirable, to utilize promoter or control sequences normally associated with the desired gene sequence, provided such control sequences are compatible with the host cell systems.

An origin of replication may be provided with by construction of the vector to include an exogenous origin, such as may be derived from SV40 or other viral (e.g., Polyoma, Adeno, VSV, BPV, CMV) source, or may be provided by the host cell chromosomal replication mechanism. If the vector is integrated into the host cell chromosome, the latter is often sufficient.

pCMV Eukaryotic Expression Vectors

The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region above each plasmid. The pCMV4 vector differs from these 4 plasmids in containing a translation enhancer in the sequence prior to the polylinker. While they are not directly derived from the pCMV1-5 series of vectors, the functionally similar pCMV6b and c vectors are available from the Chiron Corp. of Emeryville, Calif. and are identical except for the orientation of the polylinker region which is reversed in one relative to the other.

The universal components of the pCMV plasmids are as follows. The vector backbone is pTZ18R (Pharmacia), and contains a bacteriophage f1 origin or replication for production of single stranded DNA and an ampicillin-resistance gene. The CMV region consists of nucleotides −760 to +3 of the powerful promote-regulatory region of the human cytomegalovirus (Towne stain) major immediate early gene (Thomsen et al., 1984; Boshart et al., 1985). The polylinker region may be synthesized on an Applied Biosystem's machine. The human growth hormone fragment (hGH) contains transcription termination and poly-adenylation signals representing sequences 1533 to 2157 of this gene (Seeburg, 1982). There is an Alu middle repetitive DNA sequence in this fragment. Finally, the SV40 origin of replication and early region promoter-enhancer derived from the pcD-X plasmid (HindII to PstI fragment) described in (Okayama et al., 1983). The promoter in this fragment is oriented such that transcription proceeds away from the CMV/hGH expression cassette.

The pCMV plasmids are distinguished from each other by which restriction enzyme sites are unique in the polylinker and by the presence or absence of the translation enhancer. The starting pCMV1 plasmid has been progressively modified to render unique an increasing number of sites in the polylinker. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'-untranslated region of a mRNA transcribed from the CMV promoter. The sequence acts as a translational enhancer by decreasing the requirements for initiation factors in protein synthesis (Jobling et al., 1987; Browning et al., 1988). To create pCMV5, a segment of DNA (HpaI to EcoRI) was deleted from the SV40 origin region of pCMV1 to render unique all sites in the starting polylinker.

The pCMV vectors have been employed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, $G_s$ alpha protein, protein phosphatase, synaptophysin, synapsin, insulin receptor, flu hemmagglutinin, androgen receptor, sterol 26-hydroxylase, steroid 17- and 21-hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites that may cause spurious translation initiation. This codon should be avoided if possible in expression plasmids. A paper describing the construction and use of the parenteral pCMV1 and pCMV4 vectors has been published (Andersson et al., 1989b).

Nucleic Acid Hybridization Embodiments

As mentioned, in certain aspects, the DNA sequence information provided by the invention allows for the preparation of relatively short DNA (or RNA) sequences having the ability to specifically hybridize to gene sequences of the selected somatostatin receptor gene. In these aspects, nucleic acid probes of an appropriate length are prepared based on a consideration of the selected somatostatin receptor sequence, e.g., a sequence such as that shown in Sequence ID Nos. 1, 3, 5, 7, 9 or 11. The ability of such nucleic acid probes to specifically hybridize to the somatostatin receptor gene sequences lend them particular utility in a variety of embodiments. Most importantly, the probes can be used in a variety of assays for detecting the presence of complementary sequences in a given sample. However, either uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 14 to 40 or so long nucleotide stretch of the somatostatin receptor sequence, such as that shown in Sequence ID Nos. 1,3,5,7,9 or 11. A size of at least 14 nucleotides in length helps to ensure that the fragment will be of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained, longer hybridizing molecules may be used. One will generally prefer to design nucleic acid molecules having gene-complementary stretches of 14 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, herein incorporated by reference, or by introducing selected sequences into recombinant vectors for recombinant production.

Accordingly, the nucleotide sequences of the invention may be used for their ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and r high temperature conditions, such as provided by 0.02M–0.15M NaC at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate somatostatin receptor coding sequences for related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one will likely desire to employ an enzyme tag such a urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Biological Functional Equivalent Amino Acids

As noted above, it is believed that, where desired, modification and changes may be made in the structure of the somatostatin receptor polypeptide and still obtain a molecule having like or otherwise desirable characteristics. Such changes may occur in natural isolates or may be synthetically introduced using site-specific mutagenesis as described below.

For example, certain amino acids may be substituted for other amino acids in a protein structure without appreciable loss of interactive binding capacity with structures such as antigen-binding regions of antibodies (or, e.g., binding sites on substrate molecules). Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even counterveiling properties (e.g., antagonistic v. agonistic). It is thus contemplated by the inventors that various changes may be made in the sequence of the peptides (or underlying DNA) without appreciable loss of their biological utility or activity.

The importance of the hydropathic index of amino acids in conferring interactive biologic function on a protein has been discussed generally by Kyte et al. (1982), or U.S. Pat. No. 4,554,101 to Hopp, both incorporated herein, wherein it is found that certain amino acids may be substituted for other amino acids having a similar hydropathic index or score and still retain a similar biological activity. As displayed in the table below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules.

TABLE I

| AMINO ACID | HYDROPATHIC INDEX |
| --- | --- |
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

It is proposed that where an amino acid has a hydropathic index of within ±2 that of the base amino acid, and more preferably within ±1, such a change should nevertheless provide a protein having a similar, and perhaps even improved, functional activity. Thus, for example, it is proposed the isoleucine, which has a hydropathic index of +4.5, can be substituted for valine (+4.2) or leucine (+3.8), and still obtain a protein having similar biologic activity. Alternatively, at the other end of the scale, it is proposed that lysine (−3.9) can be substituted for arginine (−4.5), and so on.

Accordingly, these amino acid substitutions are generally based on the relative similarity of R-group substituents, for example, in terms of size, electrophilic character, charge, and the like. In general, exemplary substitutions which take various of the foregoing characteristics into consideration include the following:

TABLE II

| Original Residue | Exemplary Substitutions |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala |

TABLE II-continued

| Original Residue | Exemplary Substitutions |
| --- | --- |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Site-Specific Mutagenesis

Site-specific mutagenesis is a technique useful in the preparation of second generation proteins, or biologically functional equivalent proteins or peptides, derived from the sequences thereof, through specific mutagenesis of the underlying DNA. As noted above, such changes may be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by Adelman et al., (1983). As will be appreciated, the technique typically employs a phage vector which exist in both a single stranded and double stranded form. Typical vectors useful in site-directed mutagenesis include vectors such as the M13 phage (Messing et al., 1981). These phage are readily commercially available and their use is generally known to those of skill in the art.

In general, site-directed mutagenesis in accordance herewith is performed by first obtaining a single-stranded vector which includes within its sequence a DNA sequence which encodes all or a portion of the somatostatin receptor polypeptide sequence selected. An oligonucleotide primer bearing the desired mutated sequence is prepared, generally synthetically, for example, by the method of Crea et al., (1978). This primer is then annealed with the singled-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutated sequence arrangement.

Screening Assays

An important aspect of the invention is the use of recombinantly produced somatostatin receptor polypeptide in screening assays for the identification of substances which may inhibit or otherwise modify or alter the function of the receptor. The use of recombinantly produced receptor is of particular benefit because the naturally occurring receptor is present in only small quantities and has proven difficult to purify. Moreover, this allows one a ready source of human receptor, and particularly, the human pancreatic islet receptor, which have heretofore been lacking. The inventors discovered that the human receptor polypeptide sequence may differ slightly from the receptor obtained from species such as mice, and moreover, that the various somatostatin receptor polypeptides (SSTRs 1-3) differ from one another. The importance of this is quite significant in that it indicates that where one seeks to identify a compound, e.g., that may function to inhibit the enzyme in humans, that one should employ human species of receptor polypeptide for the screening assay, in particular, one may wish to employ the specific human SSTR of interest.

The screening assays of the invention, in preferred embodiments, will conveniently employ the receptor polypeptide directly from the recombinant host in which it is produced. This is achieved most preferably by simply expressing the selected polypeptide within the recombinant host, typically a eukaryotic host, followed by preparing a crude homogenate which includes the enzyme. A portion of the crude homogenate is then admixed with an appropriate effector of the receptor, e.g., somatostatin, octreotide, etc. (see e.g., Lamberts, et al., The Role of Somatostatin and Its Analogs in the Diagnosis and Treatment of Tumors, *Endocrine Reviews* 12(4):450–482, incorporated specifically by reference herein), along with the candidate substance to be tested. By comparing the binding of the selected effector in the presence or absence of the candidate substance, one can obtain information regarding the binding properties of the candidate substance.

In that most such screening assays in accordance with the invention will be designed to identify agents useful in mimicking the desirable aspects of somatostatin while eliminating the undesirable aspects of the hormone, preferred assays will employ somatostatin as the normal effector.

There are believed to be a wide variety of embodiments which can be employed to determine the effect of the candidate substance on the receptor polypeptides of the invention, and the invention is not intended to be limited to any one such method. However, it will generally be desirable to employ a system wherein one can measure the ability of the receptor polypeptide to bind to and or be modified by the effector employed to a particular substance. One method which may be employed may use a labeled effector, which has been labeled in a manner such that the label is quantitatively retained in the resultant effector/receptor complex. A convenient approach is the use of a radioactive label, such as $^{125}I$, $^{14}C$ or $^{3}H$, which may be directly quantitated in both the effector and the resultant complex.

In preferred assays, the admixture containing the protein, effector and candidate substance is allowed to incubate for a selected amount of time, and the resultant incubated mixture subjected to a separation means in order to separate the unbound effector remaining in the admixture from any effector/receptor complex so produced. Then, one simply measures the amount of each, e.g., versus a control to which no candidate substance has been added. This measurement can be made at various time points where velocity data is desired. From this, one may determine the ability of the candidate substance to alter or modify the function of the receptor.

Numerous techniques are known which could be employed for the separation of the effector from effector/receptor complex, and all such methods are intended to fall within the scope of the invention. Use of thin layer chromatographic methods (TLC), HPLC, spectrophotometric, gas chromatographic/mass spectrophotometric or NMR analyses. It is contemplated that any such technique may be employed so long as it is capable of differentiating between the effector and complex, and can be used to determine enzymatic function such as by identifying or quantifying the substrate and product.

The effector/receptor complex itself may also be the subject of techniques such as x-ray crystallography. Where a candidate substance replaces the effector molecule as the drug's mode of action, studies designed to monitor the replacement and its effect on the receptor will be of particular benefit.

EXAMPLES

Examples have been included in order to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

EXAMPLE I: CLONING AND EXPRESSION OF SSTR1

Cloning Techniques

Methods were carried out as described in Sambrook et al. (1989) and described previously (Fukumoto et al. 1988). Human pancreatic islets were obtained by ASM digestion and Ficoll purification using a sterile preparation, frozen in aliquots of 20,000 islets per tube and maintained at −70 degrees C. (such materials may be most easily obtained from the Islet Transplantation Laboratory, Washington University Medical School, St. Louis, Mo. 63110). RNA was isolated using the guanidinium thiocyanate/CsCl procedure (Sambrook, et al. 1989). DNA sequencing was done by the dideoxynucleotide chain-termination procedure (Sanger et al. 1980) after subcloning appropriate DNA fragments into M13mp18 or 19. Both strands were sequenced.

Ten $\mu$g of total human pancreatic islet RNA were reverse transcribed using an oligo (dT) primer and AMV-reverse transcriptass (Molecular Biological Resources, Tampa, Fla.). Sequences related to G protein-coupled receptors were amplified using PCR and the degenerate oligonucleotide primers described in Libert et al. 1989. The PCR products were separated on a 1% low melting temperature agarose gel and DNA fragments between 400 and 500 base pairs were eluted from the agarose, ligated into M13mp18 and sequenced. The PCR product encoding a novel G proteincoupled receptor, termed hGPR81, was $^{32}P$-labeled by nicktranslation and used to screen a human genomic library (Lawn et al. 1978) and to isolate the gens encoding this new member of the seven-transmembrane family of receptors. Standard hybridization conditions were used [42° C.; 16 h; 50% formamide, 5×SSC, 2×Denhardt's solution, 20 mM sodium phosphate buffer, pH 6.5, 0.1% sodium dodecyl sulfate, 100 μg/ml sonicated and denatured salmon testes DNA, and 10% dextran sulfate (Kayano et al. 1988)] and filters were washed at 50° C. in 0.1×SSC and 0.1% SDS before autoradiography. Mouse SSTR1 and human and mouse SSTR2 genes were isolated from human and mouse genomic libraries (Stratagene, LaJolla, Calif.) by hybridization as described above.

Expression Techniques

At 1.5 PstI/XmnI fragment of the human SSTR1 gene and a 1.2 kb XbaI fragment of the mouse SSTR2 gene were inserted into the mammalian expression vectors pCMV6b and 6c, respectively (a gift of Dr. B. Chapman, Chiron Corp., Emeryville, Calif.). The resulting constructs were co-transfected with pSV2neo into the dihydrofolate reductase-deficient Chinese hamster ovary (CHO) cell line, DG44, using Lipofectin Reagent (GIBCO BRL, Gaithersburg, Md.). Stable transfectants were selected and maintained in α-MEM (GIBCO BRL) containing 400 μg/ml G418. Each cell line was grown to confluency in 6-well, 35-mm diameter plates at 37° C. The cells were washed with buffer containing 10 mM HEPES, 5 mM $KH_2PO_4$, 5 mM $MgCl_2$, 150 mM NaCl and 1% (w/v) bovine serum albumin (all at pH 7.4), and were stabilized in the same buffer for 30 min at 22° C. Cells were incubated in duplicate with 1 ml of buffer containing bacitracin (1 mg/ml) and [[$I^{125}$]-iodo-Tyr$^{11}$]-somatostatin-14 (50,000 cpm, Amersham, Arlington Heights, Ill.) alone, or with somatostatin-14 or somatostatin-28 (Bachem, Philadelphia, Pa.) at the concentrations indicated in FIG. 3 for 30 min at 22° C. Incubated cells were washed twice with 2-ml portions of ice-cold buffer and were dissolved in 1 ml of 8M urea in 3M acetic acid. The suspended cells were transferred to a tube, the well was washed with 1 ml of the same solution, and the combined extracts were measured for radioactivity by use of a gamma-counter.

Cloning Results

Messenger RNA sequences in human pancreatic islet RNA which encode G protein-coupled receptors were amplified using PCR as described above. The PCR products were cloned and sequenced and clones encoding two new putative receptors were obtained, termed hGPR81 and i5. Of 24 different clones that were sequenced, 19 encoded hGPR81 and three hGPRi5; the sequences of the remaining two clones were unrelated to those of members of the G protein-coupled receptor superfamily (Dohlman et al. 1991). As genes coding G protein-coupled receptors often lack introns (Kobika et al. 1987), the genes encoding these two new receptors were isolated and sequenced. The sequence of the genomic fragment encoding hGPR81 revealed a 1,173 bp open reading frame (FIG. 1A) encoding a 391-aminoacid protein, $M_r$=42,657.

This protein has seven putative transmembrane domains and the extracellular $NH_2$-terminal segment preceding the first membrane-spanning segment has three consensus sites for N-linked glycosylation (Asn$^4$, Asn$^{44}$, and Asn$^{48}$). There are two putative phosphorylation sites for cyclic AMP-dependent protein kinase (Kemp et al. 1990) (Thr$^{172}$ and SEr$^{265}$) in regions that are predicted to be intracellular. The intracellular COOH-terminal domain is also serine- and threonine-rich and could serve as a substrate for serine/threonine protein kinases (Sibley et al. 1987). In addition, several amino acids that are conserved within the superfamily of G protein-coupled receptors (Dohlman et al. 1991; Findlay et al. 1990) are also conserved in hGPR81 (FIG. 2).

To confirm that hGPR81 was encoded by a gene that lacked introns, the gene for the mouse homolog was isolated and sequenced. There is 99% identity between the amino acid sequences of the human and mouse proteins (FIG. 1A). This high degree of sequence identity suggests that all domains of this protein are functionally important.

Expression Results

Since the presence of a short cytoplasmic loop connecting transmembrane segments M5-M6 is a feature of G protein-coupled receptors that bind peptide hormones and neuropeptides (E. M. Ross 1990), peptides known to regulate hormone secretion from pancreatic islets were tested as ligands for hGPR81. Initial attempts to identify the ligand for hGPR81 by injecting RNA transcribed in vitro into Xenopus laevis oocytes (Kayano et al. 1990) and assessing changes in basal or stimulated cAMP levels in response to virus peptides [calcitonin-gene-related peptide, gastric inhibitory polypeptide, glucagon, glucagon-like peptide 1-(7-36 amide), and vasoactive intestinal peptide], or $Ca^{2+}$ efflux (Williams et al. 1988) (angiotensin II, bombesin, cholecystokinin, and vasopressin) were unsuccessful. The binding of radiolabeled peptides (galanin, glucagon and somatostatin) to COS-7 cells transiently expressing hGPR81 was attempted, as well. When transfected cells were incubated with [[$I^{125}$]iodo-Tyr$^{11}$]-somatostatin-14 and the plates subjected to autoradiography, positive signals were detected that could be competed by addition of excess unlabeled somatostatin-14 suggesting that hGPR81 was a somatostatin receptor, and was designated SSTR1.

The pharmacological characteristics of SSTR1 were examined in CHO cells that were stably expressing this receptor. These cells exhibited specific binding of [[$I^{125}$]iodo-Tyr$^{11}$]-somatostatin-14 (FIG. 3A) with a higher affinity for somatostatin-14 than somatostatin-28, having inhibitory concentration for half-maximum response ($IC_{50}$) values of 1.5 and 4.7 nM, respectively. These values are similar to those reported previously for the affinity of somatostatin-14 and -28 for their native receptors (Srikant et al. 1981; Tran et al. 1985; Schonbrunn et al. 1983).

EXAMPLE II: CLONING AND EXPRESSION OF SSTR2

Cloning Techniques and Results

Figure 4:
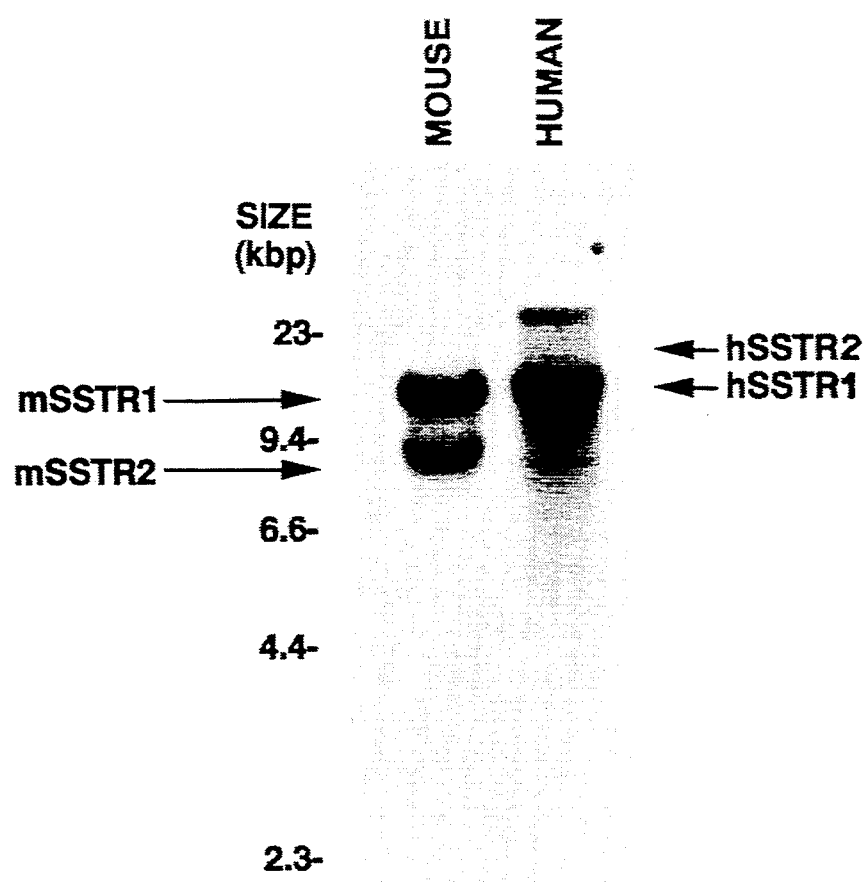
FIG. 4. Southern blot analysis of human and mouse genomic DNA. Ten µg of human and mouse genomic DNA were digested with EcoRI, electrophoresed in a 1% agarose gel, blotted onto a nitrocellulose filter and hybridized with a $^{32}$P-labeled human SSTR1 probe as described in Materials and Methods. The EcoRI fragments containing human and mouse SSTR1 and 2 genes are indicated by arrows.

Hybridization of a human SSTR1 probe to a Southern blot of EcoRI-digested human DNA showed a strong signal at 14 kb, the size expected for the EcoRI fragment containing this gene, as well as weaker hybridization to fragments of >23, 18, 8.4, and 7.8 kb (FIG. 4). This probe also hybridized to multiple fragments in an EcoRI digest of mouse DNA of >23, 13.5, 8.6, and 8.2 kb. The presence of hybridizing fragments, in addition to those expected, suggested that there was a family of somatostatin receptors as noted previously for the adrenergic and dopaminergic receptors (Kobilka et al. 1987; Bunzow et al. 1988).

By screening human and mouse genomic libraries with a human SSTR1 probe, we isolated the gene encoding a second putative somatostatin receptor, termed SSTR2; the EcoRI fragments containing the human and mouse SSTR2 genes are 18 and 8.2 kb, respectively, and noted in FIG. 4. The nucleotide sequence of the human SSTR2 gene revealed a 1,107 bp open reading frame, encoding a 369-amino-acid protein ($M_4=41,305$) (FIG. 1B) that has seven transmembrane segments, four putative N-glycosylation sites ($Asn^9$, $Asn^{22}$, $ASn^{29}$, and $Asn^{32}$) in the extracellular NH$_2$-terminal segment, and one that could be phosphorylated by a cAMP-dependent protein kinase (Kobilka et al. 1987) ($Ser^{250}$). There is 94% identity between the amino acid sequences of human and mouse SSTR2 (FIG. 1B).

Figure 3B:
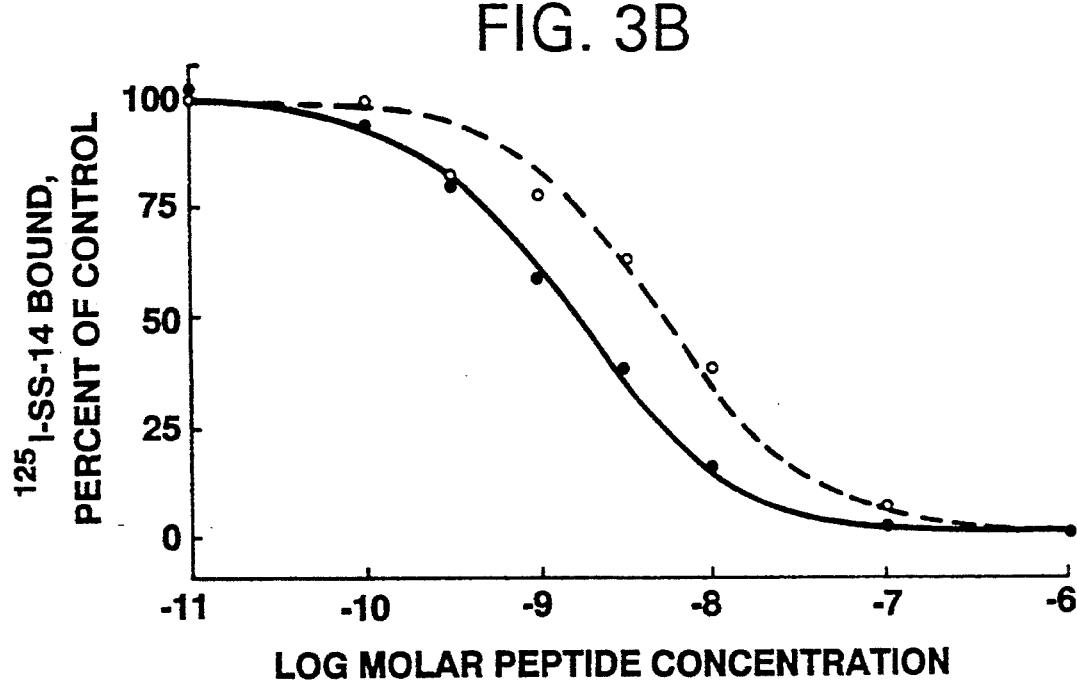

Comparison of the amino acid sequences of human SSTR1 and 2 indicates that there is 46% identity and 70% similarity between these two receptors (FIG. 2). The regions of greatest identity are the transmembrane domains, especially M1, M2, and M7, implying that perhaps these regions may be involved in ligand binding. The pharmacological properties of SSTR2 are similar to those of SSTR1 with a higher affinity for somatostatin-14 and -28. The IC$_{50}$ values are 1.6 and 5.2 nM, respectively (FIG. 3B).

Expression Techniques and Results

Figure 5A:
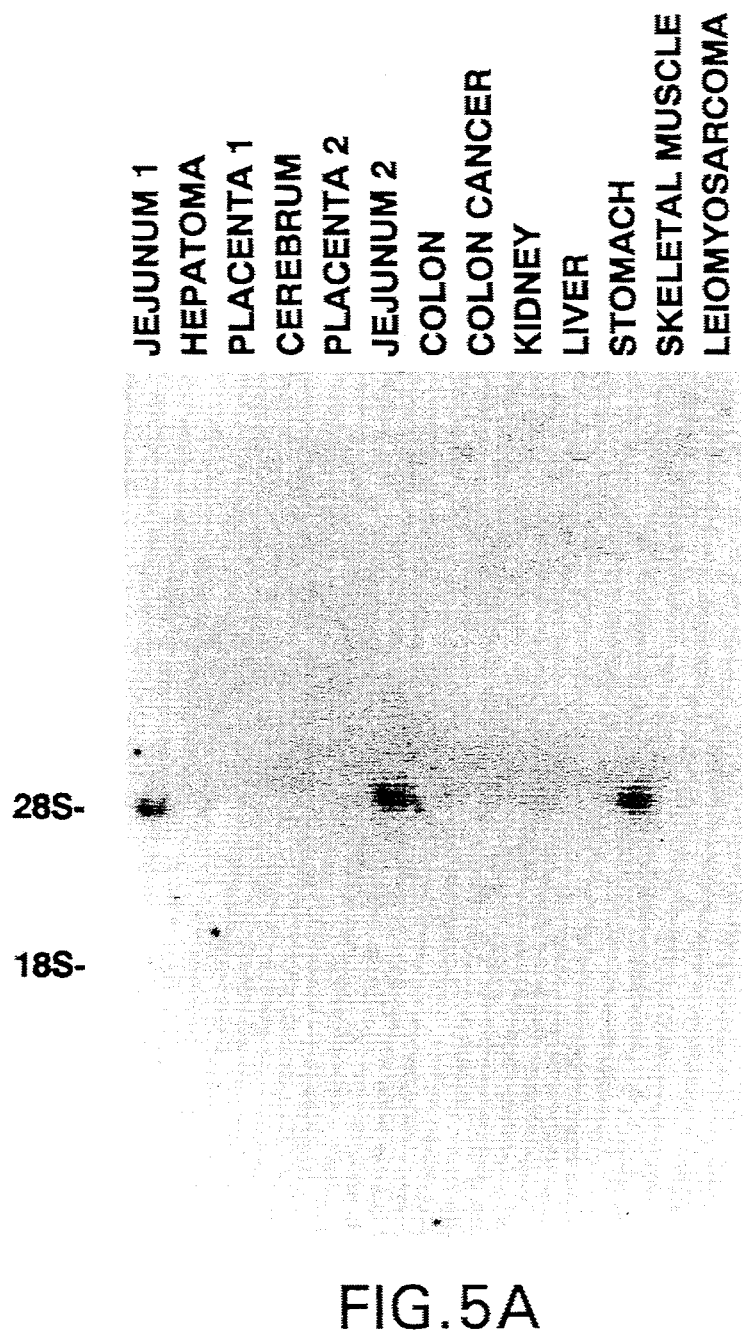
FIGS. 5A and 5B. Northern blot analyses of SSTR1 and SSTR2 mRNA in human tissues. Twenty µg of total RNA were denatured with glyoxal, electrophoresed in a 1% agarose gel, blotted onto a nylon membrane and hybridized with $^{32}$P-labeled human SSTR1 (A) or human SSTR2 (B) probes.
Figure 5B:
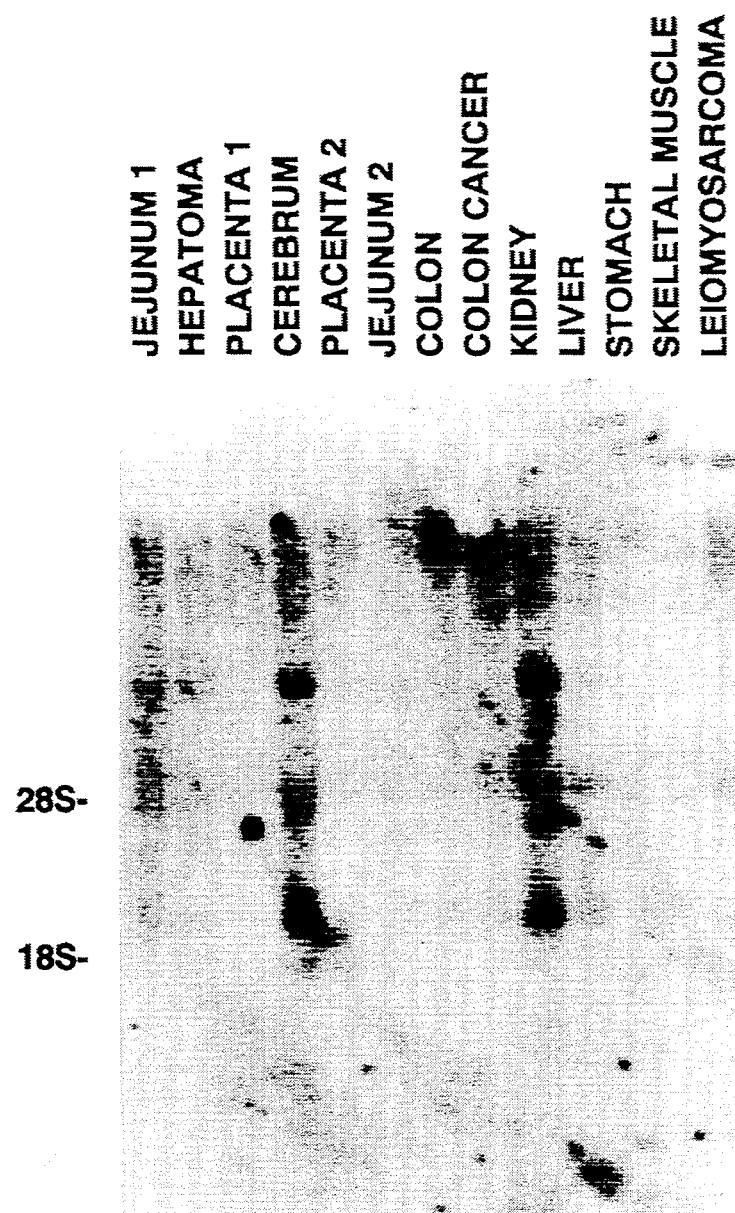

The tissue distribution of SSTR1 and 2 was examined by RNA blotting. Human SSTR1 mRNA was 4.8 kb in size and was expressed at highest levels in jejunum and stomach (FIG. 5A); it was also readily detected in human islet RNA (data not shown). There were low levels of SSTR1 mRNA in colon, colon carcinoma and kidney. Although SSTR1 mRNA could not be detected in Northern blots of human cerebrum RNA prepared from a part of the temporal lobe, it can be readily seen in blots of RNA prepared from the entire mouse brain indicating that this receptor subtype was expressed in brain (data not shown). The tissue distribution of SSTR2 was quite different from that of SSTR1. Human SSTR2 mRNA was expressed at highest levels in cerebrum and kidney and in both tissues, two transcripts of 8.5 and 2.5 kb hybridized with the SSTR2 probe (FIG. 5B). Low levels of SSTR2 mRNA were detected in jejunum, hepatoma, colon, colon carcinoma and liver. SSTR2 mRNA was also present in rat pancreatic islets (data not shown) implying that pancreatic islets express both SSTR1 and 2.

The present results indicate that the biological effects of somatostatin are mediated by tissue-specific expression of a family of somatostatin receptors. Cloning and Southern blotting studies suggest that this gene family may comprise perhaps four members. The sequences and ligand-binding properties of two of these receptors, SSTR1 and 2, have been determined. Although both possess a similar affinity for somatostatin-14 and -28, their sequences are surprisingly divergent. This sequence divergence may well underlie the diverse biological effects of somatostatin (S. Reichlin 1983) by coupling its receptors to different intracellular effector systems (Dorflinger et al. 1983; Wang et al. 1989). The cloning of SSTR1 and SSTR2 should lead to a better understanding of the molecular basis for somatostatin receptor heterogeneity as determined by cross-linking analyses (Susini et al. 1986; Sakamoto et al. 1988; Kimura et al. 1989; Thermos et al. 1990) and the mechanisms and regulation of somatostatin function. In addition, they should facilitate the development of selective analogues for specific diagnostic and therapeutic applications (A. V. Schally 1988; Lamberts et al. 1990).

EXAMPLE III: CLONING AND EXPRESSION OF SSTR3

In a manner similar to the cloning expression of SSTR2, hybridization of a human SSTR1 probe to a Southern blot of EcoRI-digested human DNA shows a strong signal at 14 kb, the size expected for the EcoRI fragment containing this gene, as well as weaker hybridizations to fragments of >23, 18, 8.4, and 7.8 kb. This probe also hybridized to multiple fragments in an EcoRI digest of mouse DNA of >23, 13.5, 8.6, and 8.2 kb. The presence of hybridizing fragments, in addition to those expected, suggested that there was a family of somatostatin receptors as noted previously for the adrenergic and dopaminergic receptors (Kobilka et al. 1987; Bunzow et al. 1988).

By screening human and mouse libraries with SSTR1 probes as described above, the genes encoding a third putative somatostatin receptor were isolated, and termed SSTR3; the EcoRI fragment containing the human SSTR3 gene is 8.4 kb while that for the mouse gene is 23 kb. The nucleotide sequence of the human SSTR3 gene revealed at least a 1254 bp open reading frame encoding a 418-amino-acid protein sequence (FIG. 6). The entire 1794 bp sequence for the mouse SSTR3 sequence was obtained as well.

EXAMPLE IV: DIAGNOSTIC/THERAPEUTIC APPLICATIONS

Given the isolation and purification of distinct somatostatin receptor proteins, it will be possible to utilize these proteins in methods designed to screen candidate substances such as candidate agonists and antagonists with potentially preferential properties for use in diagnostic and therapeutic applications.

For instance, as noted recently by (Dohlman et al. 1991) with the growing number of receptor sub-types, G proteins, and effectors, characterization of ligand binding and G protein recognition properties of receptors is an important challenge for the diagnostic and therapeutic industries. As noted therein, reconstitution experiments were the first to show that receptors can, with varying degrees of specificity, couple to multiple (and in some cases functionally distinct) G proteins (Kanaho et al. 1984;

For instances, cloning and overproduction of the muscarinic and $\alpha_2$-ARs led to the demonstration that a single receptor subtype, when expressed at high levels in the cell, will couple to more than one type of G protein. For each of these receptors, agonists treatment led to both inhibition of adenylyl cyclase and stimulation of phosphoinositide metabolism. Finally, individual G proteins species have been shown to stimulate more than one effector, $G_s$, for example, has been reported to regulate calcium channels, in addition to adenylyl cyclase. These authors note that given this complexity and apparent degeneracy of function, a question of fundamental importance is how, and under what circumstances, can G proteins organize signals from multiple receptors and direct them to the appropriate effectors?

The traditional approach has been to reconstitute the purified receptor and G protein components in vitro. Unfortunately, as noted by these authors, purification schemes have been successful for only a very limited number of receptor sub-types and there cognate G-proteins. Alternatively, and as here enabled by the cloning and sequencing of the somatostatin receptors identified thus far, heterologous expression systems may be of more general usefulness in the characterization of cloned receptors and in elucidating receptor-G protein coupling specificity.

Once such system has been recently developed in yeast cells, in which genes for a mammalian $\beta_2$-AR and $G_s$ $\alpha$-subunit were coexpressed (King et al. 1990). Expression of the $\beta_2$-AR to levels several hundred-fold higher than any human tissue was attained, and ligand binding was shown to be of the appropriate affinity, specificity, and stereoselectivity. Moreover, a $\beta_2$-AR-mediated activation of the pheromone signal transduction pathway was demonstrated by several criteria, including altered growth rates, morphological changes, and induction of a pheromone-responsive promoter (FUS1) fused to the Escherichia coli lacZ gene (encoding $\beta$-galactosidase).

The ability to control the yeast pheromone response pathway by expression of the $\beta_2$-AR and $G_s$ $\alpha$ has the potential to greatly facilitate structural and functional characterization of such receptors. By scoring for growth rates or $\beta$-galactosidase induction, the properties of mutant receptors can be tested rapidly. In addition, isolated recombinant somatostatin receptors as enabled herein should be capable of discriminating candidate substances with the desirable properties of somatostatin, which however lack the undesirable properties of somatostatin such as inhibition of insulin or glugacon release and vice versa. Furthermore, it should be possible using systems such as that described above to identify candidate substances having selective ability to interact with one or more of the somatostatin receptor proteins enabled by the present application over others in the same family of somatostatin receptors.

Thus, for instance, it will be possible to utilize a battery of somatostatin receptors cloned and expressed in a particular common cell line and to expose such a battery of receptor proteins to a variety of candidate substances. The results of such a screening assay should be capable of identifying a candidate substance capable of, for instance, interacting with SSTR1, which candidate substance does not interact with SSTR2 or SSTR3.

Furthermore, it should be possible then to investigate the structure-activity relationships of somatostatin when compared to the isolated recombinant somatostatin receptors enabled by the present application. Such studies would include not only binding studies to identify candidate substances such as agonists and antagonists which will bind each individual somatostatin receptor, but will also include studies to identify those candidate substances which stimulate an activity in the somatostatin receptor apart from the binding of the same to the receptor.

Moreover, as noted by Dohlman et al. 1991, as additional genes for the putative G-proteins, coupled receptors, such as those enabled by the present application, are isolated, a series of ligands can be conveniently screened to identify those with activity toward the unidentified gene product. As noted by these authors as well, expression of a single receptor in the absence of other related sub-types is often impossible to achieve in native mammalian cells. Thus, expression in a microorganism, or in an isolated eukaryotic cell that has no such endogenous receptors can be useful for screening and evaluating sub-type-selective drugs (Marullo et al. 1988; Payette et al. 1990; and King et al. 1990).

Therapies using the compositions and methods of the present invention are also possible. Lamberts, et al., The Role of Somatostatin and Its Analogs in the Diagnosis and Treatment of Tumors, Endocrine Reviews 12(4):450–482, incorporated specifically by reference herein, outlines at least some of the potential diagnostic and therapeutic procedures available. Thus, as can be seen therein, a number of human tumors have been detected which possess human somatostatin receptors. Such tumors include: pituitary tumors; endocrine pancreatic tumors; carcinoids; other "APUDomas" including paragangliomas, pheochromomcytomas, medullary thyroid carcinomas, and small cell lung cancer; neuroblastomas; brain tumors including meningiomas and glia-derived brain tumors; Merkel cell tumors; breast cancer; adenocarcinomas; as well as, lymphomas and "activated" leucocytes.

REFERENCES CITED

The references listed below are incorporated herein by reference to the extent that they supplement, explain, provide a background for or teach methodology, techniques and/or compositions employed herein.

Adelman et al. (1983) DNA 2:183.
Andersson, et al. (1989) J. Biol. Chem. 264:8222.
Bolivar et al., (1977) Gene, 2:95.
Boshart et al. (1985) Cell 41:521.
Brown (1990) Annu. Rev. Physiol. 52:197.
Browning et al. (1988) JBC 263:9630.
Bunzow, J.R. (1988) Nature (London) 336:783.
Cerione et al. (1985) J. Biol. Chem. 260:1493.
Chang et al., (1978) Nature, 375:615.
Connolly et al. (1989) Cell 57:599.
Cotecchia et al. (1988) Proc. Ntl. Acad. Sci. USA 85:7159.
Cotecchia et al. (1990) Proc. Ntl. Acad. Sci. USA 87:2896.
Crea et al., (1978) Proc. Natl. Acad. Sci. U.S.A, 75:5765.
Dixon et al. (1986) Nature 321:75.
Dohlman (1987) Biochemistry 26:2657.
Dohlman, H. G. (1991) Annu. Rev. Biochem. 60:166–170; 174–s176; 653–688.
Dolphin (1990) Annu. Rev. Physiol. 52:243.
Dorflinger, L. J. et al. (1983) Endocrinology 3:1551.
Emotine et al. (1989) Science 245:1118.
EPO Appl. Publ. No. 0036776.
Esch, F. et al. (1980) Proc. Natl. Acad. Sci. USA 77:6827.
Fiers et al., (1978) Nature 273:113.
Findlay, J. et al. (1990) Trends Pharmacol. Sci. 11:492.
Frielle et al. (1987) Proc. Ntl. Acad. Sci. USA 84:7920.
Fukumoto, H. et al. (1988) Proc. Natl. Acad. Sci. USA 85:5434.
Goeddel et al., (1979) Nature, 281:544.
Goeddel et al., (1980) Nucleic Acids Res., 8:4057.
He et al. (1989) Proc. Ntl. Acad. Sci. USA 86:1480.
Hess et al., (1968) J. Adv. Enzyme Reg. 7:149.
Hitzeman et al., (1980) J. Biol. Chem. 255:2073.
Holland et al., (1978) Biochemistry 7:4900.
Hubbard et al. (1958) Proc. Ntl. Acad. Sci. USA 44:130.
Itakura et al., (1977) Science, 198:1056.
Itoh et al. (1988) J. Biol. Chem. 263:6656.
Jobling et al. (1987), Nature 325:622.
Jones, (1977) Genetics 85:12.

Kanaho et al. (1984) *J. Biol. Chem.* 259:7378.
Kayano, T. et al. (1988) *J. Biol. Chem.* 263:15245.
Kayano, T. et al. (1990) *J. Biol. Chem.* 265:13276.
Kemp, B. E. et al. (1990) *Trends Biochem. Sci.* 15:342.
Kimura et al. (1989) *J. Biol. Chem.* 264:7033.
King et al. (1990) *Science* 250:121.
Kingsman et al., (1979) *Gene*, 7:141.
Kobilka, B. K. et al. (1987) *J. Biol. Chem.* 262:7321.
Kozasa et al. (1988) *Proc. Ntl. Acad. Sci USA* 85:2081.
Kruse and Patterson, eds. (1973) *Tissue Culture*, Academic Press.
Kyte, J., and R. F. Doolittle (1982) *J. Mol. Biol.* 157:105.
Lamberts, S. W. J. et al. (1990) *N. Engl. J. Med.* 323:1246.
Lawn, R. M. et al. (1978) *Cell* 5:1157.
Lewis, D. L. et al. (1985) *Proc. Natl. Acad. Sci. USA* 83:9035.
Libert, F. et al. (1989) *Science* 244:569.
Lomasney et al. (1990) *Proc. Ntl. Acad. Sci. USA* 87:5094.
Marullo et al. (1988) *Proc. Ntl. Acad. Sci. USA* 85:7551.
Messing et al., Third Cleveland Symposium on Macromolecules and Recombinant DNA, Editor A. Walton, Elsevier, Amsterdam (1981).
Moss et al. (1988) *Adv. Enzymol.* 61:303.
Nathans et al. (1986 A) *Science* 232:193.
Nathans et al. (1986 B) *Science* 232:203
Okayama et al. (1983) *MCB* 3:280.
Payette et al. (1990) *FEBS Lett.* 266:21.
Patel et al. (1990) *Metabolism* 39:63.
Peralta et al. (1988) *Nature* 334:434.
Pradayrol, et al., (1980) *FEBS Lett.* 109:55.
Regan et al. (1988) *Proc. Ntl. Acad. Sci. USA* 85:6301.
Reichlin, S., *N. Engl. J. Med.* (1983) 309:1495-1551, 1556-1563.
Reisine et al. (1985) *J. Pharmacol. Exp. Ther.* 232:275.
Reyl-Desmars et al. (1989) *J. Biol. Chem.* 264:18789.
Ross, E. M. (1990) *Nature (London)* 344:707.
Sakamoto, C. (1988) *J. Biol. Chem.* 263:14441.
Sambrook, J. et al. (1989) *Molecular Cloning: A Laboratory Manual* (Cold Spring Harbor Laboratory Press, Cold Spring Harbor, N.Y.).
Sanger, F. et al. (1980) *J. Mol. Biol.* 142:161.
Schally, A. V. (1988) *Cancer Res.* 48, 6977.
Schonbrunn, A. et al. (1983) *Endocrinology* 113:1559.
Schultze et al. (1990) *Annu. Rev. Physiol.* 52:275.
Schwinn et al. (1990) *J. Biol. Chem.* 265:8183.
Seeburg (1982) *DNA* 1:239.
Senogles et al. (1990) *J. Biol. Chem.* 265:4507.
Shen, L-P. et al., (1982) *Proc. Natl. Acad. Sci. USA* 79:4575.
Sibley, D. R. (1987) *Cell* 48:913.
Siebwenlist et al., (1980) *Cell*, 20:269.
Srikant, C. B. & Patel, Y. C. (1981) *Nature (London)* 294:259.
Stinchcomb et al., (1979) *Nature*, 282:39.
Susini, C. et al. (1986) *J. Biol. Chem.* 261:16738.
Szabo et al. (1990) *Annu. Rev. Physiol.* 52:293.
Thermos, K. et al. (1990) *Am. J. Physiol*, 259, E216.
Thomsen et al. (1984) *PNAS* 81:659.
Tran, V.T. et al. (1985) *Science*, 228:492.
Trautwein et al. (1990) *Annu. Rev. Physiol.* 52:257.
Tsai et al. (1984) *J. Biol. Chem.* 259:15320.
Tschemper et al., (1980) *Gene* 10:157.
Wald (1968) *Nature* 219:800.
Wang, H.-L. et al. (1989) *Proc. Natl. Acad. Sci. USA* 86:9616.
Wass, J. A. H., (1989) in *Endocrinology*, ed. DeGroot, L. J. (W. B. Saunders, Philadelphia, Pa.), 1:152.
Wheeler et al. (1977) *Proc. Ntl. Acad. Sci. USA* 74:4238.
Williams, J. A. et al. (1988) *Proc. Natl. Acad. Sci. USA* 85:4939.

---

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1634 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
CTGCAGGCAA  GCGGTCGGGT  GGGGAGGGAG  GGCGCAGGCG  GCGGGTGCGC  GAGGAGAAAG       60

CCCCAGCCCT  GGCAGCCCCA  CTGGCCCCCC  TCAGCTGGGA  TGTTCCCCAA  TGGCACCGCC      120

TCCTCTCCTT  CCTCCTCTCC  TAGCCCCAGC  CCGGGCAGCT  GCGGCGAAGG  CGGCGGCAGC      180

AGGGGCCCCG  GGGCCGGCGC  TGCGGACGGC  ATGGAGGAGC  CAGGGCGAAA  TGCGTCCCAG      240

AACGGGACCT  TGAGCGAGGG  CCAGGGCAGC  GCCATCCTGA  TCTCTTTCAT  CTACTCCGTG      300

GTGTGCCTGG  TGGGGCTGTG  TGGGAACTCT  ATGGTCATCT  ACGTGATCCT  GCGCTATGCC      360

AAGATGAAGA  CGGCCACCAA  CATCTACATC  CTAAATCTGG  CCATTGCTGA  TGAGCTGCTC      420

ATGCTCAGCG  TGCCCTTCCT  AGTCACCTCC  ACGTTGTTGC  GCCACTGGCC  CTTCGGTGCG      480
```

| | | | | |
|---|---|---|---|---|
| CTGCTCTGCC | GCCTCGTGCT | CAGCGTGGAC | GCGGTCAACA | TGTTCACCAG | CATCTACTGT | 540 |
| CTGACTGTGC | TCAGCGTGGA | CCGCTACGTG | GCCGTGGTGC | ATCCCATCAA | GGCGGCCCGC | 600 |
| TACCGCCGGC | CCACCGTGGC | CAAGGTAGTA | AACCTGGGCG | TGTGGGTGCT | ATCGCTGCTC | 660 |
| GTCATCCTGC | CCATCGTGGT | CTTCTCTCGC | ACCGCGGCCA | ACAGCGACGG | CACGGTGGCT | 720 |
| TGCAACATGC | TCATGCCAGA | GCCCGCTCAA | CGCTGGCTGG | TGGGCTTCGT | GTTGTACACA | 780 |
| TTTCTCATGG | GCTTCCTGCT | GCCCGTGGGG | GCTATCTGCC | TGTGCTACGT | GCTCATCATT | 840 |
| GCTAAGATGC | GCATGGTGGC | CCTCAAGGCC | GGCTGGCAGC | AGCGCAAGCG | CTCGGAGCGC | 900 |
| AAGATCACCT | TAATGGTGAT | GATGGTGGTG | ATGGTGTTTG | TCATCTGCTG | GATGCCTTTC | 960 |
| TACGTGGTGC | AGCTGGTTAA | CGTGTTTGCT | GAGCAGGACG | ACGCCACGGT | GAGTCAGCTG | 1020 |
| TCGGTCATCC | TCGGCTATGC | CAACAGCTGC | GCCAACCCCA | TCCTCTATGG | CTTTCTCTCA | 1080 |
| GACAACTTCA | AGCGCTCTTT | CCAACGCATC | CTATGCCTCA | GCTGGATGGA | CAACGCCGCG | 1140 |
| GAGGAGCCGG | TTGACTATTA | CGCCACCGCG | CTCAAGAGCC | GTGCCTACAG | TGTGGAAGAC | 1200 |
| TTCCAACCTG | AGAACCTGGA | GTCCGGCGGC | GTCTTCCGTA | ATGGCACCTG | CACGTCCCGG | 1260 |
| ATCACGACGC | TCTGAGCCCG | GGCCACGCAG | GGGCTCTGAG | CCCGGGCCAC | GCAGGGGCCC | 1320 |
| TGAGCCAAAA | GAGGGGGAGA | ATGAGAAGGG | AAGGCCGGGT | GCGAAAGGGA | CGGTATCCAG | 1380 |
| GGCGCCAGGG | TGCTGTCGGG | ATAACGTGGG | GCTAGGACAC | TGACAGCCTT | TGATGGAGGA | 1440 |
| ACCCAAGAAA | GGCGCGCGAC | AATGGTAGAA | GTGAGAGCTT | TGCTTATAAA | CTGGGAAGGC | 1500 |
| TTTCAGGCTA | CCTTTTTCTG | GGTCTCCCAC | TTTCTGTTCC | TTCCTCCACT | GCGCTTGCTC | 1560 |
| CTCTGACCCT | CCTTCTATTT | TCCCCACCCT | GCAACTTCTA | TCCTTTCTTC | CGCACCGTCC | 1620 |
| CGCCAGTGCA | GATC | | | | | 1634 |

( 2 ) INFORMATION FOR SEQ ID NO:2:

( i ) SEQUENCE CHARACTERISTICS:
        ( A ) LENGTH: 391 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Phe Pro Asn Gly Thr Ala Ser Ser Pro Ser Ser Ser Pro Ser Pro
 1               5                  10                  15

Ser Pro Gly Ser Cys Gly Glu Gly Gly Ser Arg Gly Pro Gly Ala
             20                  25                  30

Gly Ala Ala Asp Gly Met Glu Glu Pro Gly Arg Asn Ala Ser Gln Asn
         35                  40                  45

Gly Thr Leu Ser Glu Gly Gln Gly Ser Ala Ile Leu Ile Ser Phe Ile
     50                  55                  60

Tyr Ser Val Val Cys Leu Val Gly Leu Cys Gly Asn Ser Met Val Ile
 65                  70                  75                  80

Tyr Val Ile Leu Arg Tyr Ala Lys Met Lys Thr Ala Thr Asn Ile Tyr
                 85                  90                  95

Ile Leu Asn Leu Ala Ile Ala Asp Glu Leu Leu Met Leu Ser Val Pro
                100                 105                 110

Phe Leu Val Thr Ser Thr Leu Leu Arg His Trp Pro Phe Gly Ala Leu
            115                 120                 125

Leu Cys Arg Leu Val Leu Ser Val Asp Ala Val Asn Met Phe Thr Ser
        130                 135                 140

Ile Tyr Cys Leu Thr Val Leu Ser Val Asp Arg Tyr Val Ala Val Val
145                 150                 155                 160
```

|  |  |  |  |  |  |  |  |  |  |  |  |  |  |  |
|---|---|---|---|---|---|---|---|---|---|---|---|---|---|---|
| His | Pro | Ile | Lys | Ala | Ala | Arg | Tyr | Arg | Arg | Pro | Thr | Val | Ala | Lys | Val |
|  |  |  | 165 |  |  |  |  | 170 |  |  |  |  | 175 |  |  |
| Val | Asn | Leu | Gly | Val | Trp | Val | Leu | Ser | Leu | Leu | Val | Ile | Leu | Pro | Ile |
|  |  |  | 180 |  |  |  |  | 185 |  |  |  |  | 190 |  |  |
| Val | Val | Phe | Ser | Arg | Thr | Ala | Ala | Asn | Ser | Asp | Gly | Thr | Val | Ala | Cys |
|  |  | 195 |  |  |  |  | 200 |  |  |  |  | 205 |  |  |  |
| Asn | Met | Leu | Met | Pro | Glu | Pro | Ala | Gln | Arg | Trp | Leu | Val | Gly | Phe | Val |
|  | 210 |  |  |  |  | 215 |  |  |  |  | 220 |  |  |  |  |
| Leu | Tyr | Thr | Phe | Leu | Met | Gly | Phe | Leu | Leu | Pro | Val | Gly | Ala | Ile | Cys |
| 225 |  |  |  |  | 230 |  |  |  |  | 235 |  |  |  |  | 240 |
| Leu | Cys | Tyr | Val | Leu | Ile | Ile | Ala | Lys | Met | Arg | Met | Val | Ala | Leu | Lys |
|  |  |  | 245 |  |  |  |  | 250 |  |  |  |  | 255 |  |  |
| Ala | Gly | Trp | Gln | Gln | Arg | Lys | Arg | Ser | Glu | Arg | Lys | Ile | Thr | Leu | Met |
|  |  |  | 260 |  |  |  |  | 265 |  |  |  |  | 270 |  |  |
| Val | Met | Met | Val | Val | Met | Val | Phe | Val | Ile | Cys | Trp | Met | Pro | Phe | Tyr |
|  |  | 275 |  |  |  |  | 280 |  |  |  |  | 285 |  |  |  |
| Val | Val | Gln | Leu | Val | Asn | Val | Phe | Ala | Glu | Gln | Asp | Asp | Ala | Thr | Val |
|  |  | 290 |  |  |  |  | 295 |  |  |  |  | 300 |  |  |  |
| Ser | Gln | Leu | Ser | Val | Ile | Leu | Gly | Tyr | Ala | Asn | Ser | Cys | Ala | Asn | Pro |
| 305 |  |  |  |  | 310 |  |  |  |  | 315 |  |  |  |  | 320 |
| Ile | Leu | Tyr | Gly | Phe | Leu | Ser | Asp | Asn | Phe | Lys | Arg | Ser | Phe | Gln | Arg |
|  |  |  |  | 325 |  |  |  |  | 330 |  |  |  |  | 335 |  |
| Ile | Leu | Cys | Leu | Ser | Trp | Met | Asp | Asn | Ala | Ala | Glu | Glu | Pro | Val | Asp |
|  |  |  | 340 |  |  |  |  | 345 |  |  |  |  | 350 |  |  |
| Tyr | Tyr | Ala | Thr | Ala | Leu | Lys | Ser | Arg | Ala | Tyr | Ser | Val | Glu | Asp | Phe |
|  |  | 355 |  |  |  |  | 360 |  |  |  |  | 365 |  |  |  |
| Gln | Pro | Glu | Asn | Leu | Glu | Ser | Gly | Gly | Val | Phe | Arg | Asn | Gly | Thr | Cys |
|  | 370 |  |  |  |  | 375 |  |  |  |  | 380 |  |  |  |  |
| Thr | Ser | Arg | Ile | Thr | Thr | Leu |  |  |  |  |  |  |  |  |  |
| 385 |  |  |  |  | 390 |  |  |  |  |  |  |  |  |  |  |

( 2 ) INFORMATION FOR SEQ ID NO:3:

( i ) SEQUENCE CHARACTERISTICS:
        ( A ) LENGTH: 1265 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
TGGAGCCTTG AGCCTAGGGA GGGCGCAGAC AGCAAGGGCG CAAGGTGAGC GCCCCAGCCG      60
GAGCCGCACC GGCCCACTTC AGCTGGGATG TTCCCCAATG CACCGCCTC  CTCTCCCTCC     120
TCTTCTCCAA GCCCCAGCCC AGGCAGCTGC GGGGAAGGAG CCTGCAGCAG GGGTCCGGGG    180
TCCGGCGCTG CGGACGGCAT GGAAGAGCCT GGACGAAACG CTTCCCAGAA TGGGACCTTA    240
AGCGAGGGAC AGGGTAGCGC CATTCTCATC TCTTTCATCT ACTCCGTGGT ATGCTTGGTG    300
GGACTGTGTG GAACTCTAT  GGTCATCTAT GTGATCCTGC GCTACGCCAA GATGAAGACC    360
GCTACCAACA TCTACATTCT AAACCTGGCT ATTGCTGATG AGCTGCTCAT GCTCAGCGTG    420
CCCTTTCTGG TCACTTCCAC GCTGTTGCGC CACTGGCCCT TCGGCGCGCT ACTTTGCCGC    480
CTGGTGCTCA GCGTGGATGC GGTCAACATG TTCACCAGCA TCTACTGTCT GACTGTGCTT    540
AGTGTGGACC GCTATGTGGC TGTGGTGCAC CCGATCAAGG CAGCGCGCTA CCGTCGGCCC    600
ACTGTGGCCA AAGTAGTGAA CCTGGGCGTG TGGGTCCTGT CATTACTGGT TATCTTGCCC    660
ATCGTGGTCT TCTCACGCAC CGCAGCCAAC AGCGATGGCA CGGTAGCCTG CAACATGCTC    720
```

```
ATGCCCGAGC CCGCCCAGCG CTGGTTGGTG GGCTTCGTCT TATACACATT TCTCATGGGC    780
TTCCTGCTGC CTGTCGGGGC CATTTGCCTG TGTTATGTGC TCATCATTGC CAAGATGCGC    840
ATGGTGGCCC TCAAGGCTGG CTGGCAGCAG CGCAAGCGCT CAGAGCGCAA GATCACTCTA    900
ATGGTGATGA TGGTGGTGAT GGTTTTTGTC ATCTGCTGGA TGCCTTTCTA CGTGGTACAG    960
CTGGTCAACG TGTTCGCCGA GCAAGACGAC GCCACCGTGA GCCAGTTGTC TGTCATCCTG   1020
GGCTATGCCA ACAGCTGTGC CAACCCCATA CTCTACGGCT TCCTGTCGGA CAACTTCAAG   1080
CGCTCTTTCC AGCGCATCCT GTGCCTCAGC TGGATGGATA ACGCTGCGGA GGAACCAGTC   1140
GACTACTATG CCACTGCCCT GAAGAGTCGA GCCTACAGCG TGGAGGACTT CCAGCCCGAG   1200
AATCTGGAGT CTGGAGGCGT TTTCCGTAAT GGCACCTGCG CTTCCAGGAT CAGCACGCTT   1260
TGAGG                                                              1265
```

(2) INFORMATION FOR SEQ ID NO:4:

(i) SEQUENCE CHARACTERISTICS:
        (A) LENGTH: 391 amino acids
        (B) TYPE: amino acid
        (D) TOPOLOGY: linear (ii) MOLECULE TYPE: protein (xi) SEQUENCE DESCRIPTION: SEQ ID NO:4:

```
Met Phe Pro Asn Gly Thr Ala Ser Ser Pro Ser Ser Ser Pro Ser Pro
 1               5                  10                  15

Ser Pro Gly Ser Cys Gly Glu Gly Ala Cys Ser Arg Gly Pro Gly Ser
            20                  25                  30

Gly Ala Ala Asp Gly Met Glu Glu Pro Gly Arg Asn Ala Ser Gln Asn
        35                  40                  45

Gly Thr Leu Ser Glu Gly Gln Gly Ser Ala Ile Leu Ile Ser Phe Ile
    50                  55                  60

Tyr Ser Val Val Cys Leu Val Gly Leu Cys Gly Asn Ser Met Val Ile
 65                  70                  75                  80

Tyr Val Ile Leu Arg Tyr Ala Lys Met Lys Thr Ala Thr Asn Ile Tyr
                 85                  90                  95

Ile Leu Asn Leu Ala Ile Ala Asp Glu Leu Leu Met Leu Ser Val Pro
                100                 105                 110

Phe Leu Val Thr Ser Thr Leu Leu Arg His Trp Pro Phe Gly Ala Leu
            115                 120                 125

Leu Cys Arg Leu Val Leu Ser Val Asp Ala Val Asn Met Phe Thr Ser
        130                 135                 140

Ile Tyr Cys Leu Thr Val Leu Ser Val Asp Arg Tyr Val Ala Val Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
                180                 185                 190

Val Val Phe Ser Arg Thr Ala Ala Asn Ser Asp Gly Thr Val Ala Cys
            195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
```

|   |   |   | 260 |   |   |   |   | 265 |   |   |   |   | 270 |   |   |
|---|---|---|---|---|---|---|---|---|---|---|---|---|---|---|---|
| Val | Met | Met | Val | Val | Met | Val | Phe | Val | Ile | Cys | Trp | Met | Pro | Phe | Tyr |
|   |   | 275 |   |   |   |   | 280 |   |   |   |   | 285 |   |   |   |
| Val | Val | Gln | Leu | Val | Asn | Val | Phe | Ala | Glu | Gln | Asp | Asp | Ala | Thr | Val |
|   | 290 |   |   |   |   | 295 |   |   |   |   | 300 |   |   |   |   |
| Ser | Gln | Leu | Ser | Val | Ile | Leu | Gly | Tyr | Ala | Asn | Ser | Cys | Ala | Asn | Pro |
| 305 |   |   |   |   | 310 |   |   |   |   | 315 |   |   |   |   | 320 |
| Ile | Leu | Tyr | Gly | Phe | Leu | Ser | Asp | Asn | Phe | Lys | Arg | Ser | Phe | Gln | Arg |
|   |   |   |   | 325 |   |   |   |   | 330 |   |   |   |   | 335 |   |
| Ile | Leu | Cys | Leu | Ser | Trp | Met | Asp | Asn | Ala | Ala | Glu | Glu | Pro | Val | Asp |
|   |   |   | 340 |   |   |   |   | 345 |   |   |   |   | 350 |   |   |
| Tyr | Tyr | Ala | Thr | Ala | Leu | Lys | Ser | Arg | Ala | Tyr | Ser | Val | Glu | Asp | Phe |
|   |   | 355 |   |   |   |   | 360 |   |   |   |   | 365 |   |   |   |
| Gln | Pro | Glu | Asn | Leu | Glu | Ser | Gly | Gly | Val | Phe | Arg | Asn | Gly | Thr | Cys |
|   | 370 |   |   |   |   | 375 |   |   |   |   | 380 |   |   |   |   |
| Ala | Ser | Arg | Ile | Ser | Thr | Leu |   |   |   |   |   |   |   |   |   |
| 385 |   |   |   |   | 390 |   |   |   |   |   |   |   |   |   |   |

( 2 ) INFORMATION FOR SEQ ID NO:5:

( i ) SEQUENCE CHARACTERISTICS:
( A ) LENGTH: 1351 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:5:

| GGATCCTTGG | CCTCCAGGGT | CCATTAAGGT | GAGAATAAGA | TCTCTGGGCT | GGCTGGAACT | 60 |
|---|---|---|---|---|---|---|
| AGCCTAAGAC | TGAAAAGCAG | CCATGGACAT | GGCGGATGAG | CCACTCAATG | GAAGCCACAC | 120 |
| ATGGCTATCC | ATTCCATTTG | ACCTCAATGG | CTCTGTGGTG | TCAACCAACA | CCTCAAACCA | 180 |
| GACAGAGCCG | TACTATGACC | TGACAAGCAA | TGCAGTCCTC | ACATTCATCT | ATTTTGTGGT | 240 |
| CTGCATCATT | GGGTTGTGTG | GCAACACACT | TGTCATTTAT | GTCATCCTCC | GCTATGCCAA | 300 |
| GATGAAGACC | ATCACCAACA | TTTACATCCT | CAACCTGGCC | ATCGCAGATG | AGCTCTTCAT | 360 |
| GCTGGGTCTG | CCTTTCTTGG | CTATGCAGGT | GGCTCTGGTC | CACTGGCCCT | TTGGCAAGGC | 420 |
| CATTTGCCGG | GTGGTCATGA | CTGTGGATGG | CATCAATCAG | TTCACCAGCA | TCTTCTGCCT | 480 |
| GACAGTCATG | AGCATCGACC | GATACCTGGC | TGTGGTCCAC | CCCATCAAGT | CGGCCAAGTG | 540 |
| GAGGAGACCC | CGGACGGCCA | AGATGATCAC | CATGGCTGTG | TGGGGAGTCT | CTCTGCTGGT | 600 |
| CATCTTGCCC | ATCATGATAT | ATGCTGGGCT | CCGGAGCAAC | CAGTGGGGGA | GAAGCAGCTG | 660 |
| CACCATCAAC | TGGCCAGGTG | AATCTGGGGC | TTGGTACACA | GGGTTCATCA | TCTACACTTT | 720 |
| CATTCTGGGG | TTCCTGGTAC | CCCTCACCAT | CATCTGTCTT | TGCTACCTGT | TCATTATCAT | 780 |
| CAAGGTGAAG | TCCTCTGGAA | TCCGAGTGGG | CTCCTCTAAG | AGGAAGAAGT | CTGAGAAGAA | 840 |
| GGTCACCCGA | ATGGTGTCCA | TCGTGGTGGC | TGTCTTCATC | TTCTGCTGGC | TTCCCTTCTA | 900 |
| CATATTCAAC | GTTTCTTCCG | TCTCCATGGC | CATCAGCCCC | ACCCCAGCCC | TTAAAGGCAT | 960 |
| GTTTGACTTT | GTGGTGGTCC | TCACCTATGC | TAACAGCTGT | GCCAACCCTA | TCCTATATGC | 1020 |
| CTTCTTGTCT- | GACAACTTCA | GAAGAGCTT | CCAGAATGTC | CTCTGCTTGG | TCAAGGTGAG | 1080 |
| CGGCACAGAT | GATGGGGAGC | GGAGTGACAG | TAAGCAGGAC | AAATCCCGGC | TGAATGAGAC | 1140 |
| CACGGAGACC | CAGAGGACCC | TCCTCAATGG | AGACCTCCAA | ACCAGTATCT | GAACTGCTTG | 1200 |
| GGGGGTGGGA | AAGAACCAAG | CCATGCTCTG | TCTACTGGCA | ATGGGCTCCC | TACCCACACT | 1260 |
| GGCTTCCTGC | CTCCCACCCC | TCACACCTGG | CTTCTAGAAT | AGAGGATTGC | TCAGCATGAG | 1320 |

TCCAATTAGA GAACGGTGTT TGAGTCAGCT T                                          1351

( 2 ) INFORMATION FOR SEQ ID NO:6:

( i ) SEQUENCE CHARACTERISTICS:
        ( A ) LENGTH: 369 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Asp Met Ala Asp Glu Pro Leu Asn Gly Ser His Thr Trp Leu Ser
  1           5                   10                  15
Ile Pro Phe Asp Leu Asn Gly Ser Val Val Ser Thr Asn Thr Ser Asn
             20                  25                  30
Gln Thr Glu Pro Tyr Tyr Asp Leu Thr Ser Asn Ala Val Leu Thr Phe
         35                  40                  45
Ile Tyr Phe Val Val Cys Ile Ile Gly Leu Cys Gly Asn Thr Leu Val
 50                  55                  60
Ile Tyr Val Ile Leu Arg Tyr Ala Lys Met Lys Thr Ile Thr Asn Ile
 65                  70                  75                  80
Tyr Ile Leu Asn Leu Ala Ile Ala Asp Glu Leu Phe Met Leu Gly Leu
             85                  90                  95
Pro Phe Leu Ala Met Gln Val Ala Leu Val His Trp Pro Phe Gly Lys
            100                 105                 110
Ala Ile Cys Arg Val Val Met Thr Val Asp Gly Ile Asn Gln Phe Thr
            115                 120                 125
Ser Ile Phe Cys Leu Thr Val Met Ser Ile Asp Arg Tyr Leu Ala Val
            130                 135                 140
Val His Pro Ile Lys Ser Ala Lys Trp Arg Arg Pro Arg Thr Ala Lys
145                 150                 155                 160
Met Ile Thr Met Ala Val Trp Gly Val Ser Leu Leu Val Ile Leu Pro
                165                 170                 175
Ile Met Ile Tyr Ala Gly Leu Arg Ser Asn Gln Trp Gly Arg Ser Ser
            180                 185                 190
Cys Thr Ile Asn Trp Pro Gly Glu Ser Gly Ala Trp Tyr Thr Gly Phe
            195                 200                 205
Ile Ile Tyr Thr Phe Ile Leu Gly Phe Leu Val Pro Leu Thr Ile Ile
        210                 215                 220
Cys Leu Cys Tyr Leu Phe Ile Ile Ile Lys Val Lys Ser Ser Gly Ile
225                 230                 235                 240
Arg Val Gly Ser Ser Lys Arg Lys Lys Ser Glu Lys Lys Val Thr Arg
                245                 250                 255
Met Val Ser Ile Val Val Ala Val Phe Ile Phe Cys Trp Leu Pro Phe
            260                 265                 270
Tyr Ile Phe Asn Val Ser Ser Val Ser Met Ala Ile Ser Pro Thr Pro
        275                 280                 285
Ala Leu Lys Gly Met Phe Asp Phe Val Val Val Leu Thr Tyr Ala Asn
    290                 295                 300
Ser Cys Ala Asn Pro Ile Leu Tyr Ala Phe Leu Ser Asp Asn Phe Lys
305                 310                 315                 320
Lys Ser Phe Gln Asn Val Leu Cys Leu Val Lys Val Ser Gly Thr Asp
                325                 330                 335
Asp Gly Glu Arg Ser Asp Ser Lys Gln Asp Lys Ser Arg Leu Asn Glu
            340                 345                 350
Thr Thr Glu Thr Gln Arg Thr Leu Leu Asn Gly Asp Leu Gln Thr Ser
```

Ile (2) INFORMATION FOR SEQ ID NO:7:

(i) SEQUENCE CHARACTERISTICS:
        (A) LENGTH: 1244 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

| | | | | | | |
|---|---|---|---|---|---|---|
| TCTAGACGGA | GTGGAAAGCA | GCCATGGAGA | TGAGCTCTGA | GCAGTTGAAT | GGGAGCCAAG | 60 |
| TGTGGGTGTC | CTCTCCATTT | GACCTCAACG | GCTCACTGGG | CCAAGCAAT | GGCTCCAACC | 120 |
| AGACCGAGCC | ATACTACGAC | ATGACAAGCA | ACGCCGTCCT | CACGTTCATC | TACTTCGTGG | 180 |
| TGTGTGTTGT | CGGGCTGTGC | GGCAACACGC | TGGTCATTTA | TGTCATCCTC | CGCTATGCCA | 240 |
| AGATGAAGAC | CATCACCAAC | ATCTACATCC | TTAACCTGGC | CATTGCAGAT | GAACTCTTCA | 300 |
| TGCTAGGGCT | TCCCTTCTTG | GCCATGCAGG | TGGCGCTAGT | CCACTGGCCT | TTTGGCAAGG | 360 |
| CCATCTGCCG | GGTGGTCATG | ACTGTAGATG | GCATCAATCA | GTTCACCAGT | ATCTTCTGCT | 420 |
| TGACGGTCAT | GAGCATCGAC | CGCTACCTGG | CCGTGGTGCA | CCCCATTAAG | TCAGCCAAAT | 480 |
| GGAGGCGACC | CCGGACAGCC | AAGATGATCA | ATGTAGCTGT | GTGGTGTGTG | TCTCTGCTCG | 540 |
| TCATTTTGCC | CATCATGATA | TACGCCGGCC | TCCGGAGCAA | CCAGTGGGGC | AGGAGCAGCT | 600 |
| GTACCATCAA | CTGGCCAGGC | GAATCCGGGG | CGTGGTACAC | AGGTTTCATT | ATCTACGCCT | 660 |
| TCATCCTGGG | GTTCCTGGTA | CCCCTTACCA | TCATTTGTCT | CTGCTACCTG | TTCATCATCA | 720 |
| TCAAGGTGAA | GTCCTCTGGA | ATCCGAGTGG | GATCATCCAA | GAGGAAAAAG | TCAGAGAAAA | 780 |
| AGGTGACCCG | CATGGTGTCC | ATCGTAGTGG | CTGTCTTCAT | CTTCTGCTGG | CTCCCCTTCT | 840 |
| ACATCTTCAA | CGTCTCTTCC | GTGTCTGTGG | CCATCAGTCC | CACCCCAGCC | CTGAAAGGCA | 900 |
| TGTTTGACTT | TGTGGTGATC | CTCACCTATG | CCAACAGCTG | CGCCAACCCC | ATCCTGTACG | 960 |
| CCTTCTTGTC | TGACAACTTC | AAGAAGAGCT | TCCAGAATGT | TCTTTGCTTG | GTCAAGGTGA | 1020 |
| GTGGTACGGA | GGATGGGGAG | AGGAGCGACA | GTAAGCAGGA | CAAATCCCGG | CTGAATGAGA | 1080 |
| CCACGGAGAC | CCAGAGGACC | CTCCTCAATG | GAGACCTCCA | AACCAGTATC | TGAACAACCC | 1140 |
| AGGAACGCAA | CATGCACACA | CACTAGCCAA | GCCCTGACTC | CTGTCAGTGT | GTCTCCATT | 1200 |
| CCCTGGCTTC | CCGCCTCCCC | TATCCATCAC | ACCCGGCTTC | TAGA | | 1244 |

(2) INFORMATION FOR SEQ ID NO:8:

(i) SEQUENCE CHARACTERISTICS:
        (A) LENGTH: 369 amino acids
        (B) TYPE: amino acid
        (D) TOPOLOGY: linear (ii) MOLECULE TYPE: protein (xi) SEQUENCE DESCRIPTION: SEQ ID NO:8:

| Met | Glu | Met | Ser | Ser | Glu | Gln | Leu | Asn | Gly | Ser | Gln | Val | Trp | Val | Ser |
|---|---|---|---|---|---|---|---|---|---|---|---|---|---|---|---|
| 1 | | | | 5 | | | | | 10 | | | | | 15 | |

| Ser | Pro | Phe | Asp | Leu | Asn | Gly | Ser | Leu | Gly | Pro | Ser | Asn | Gly | Ser | Asn |
|---|---|---|---|---|---|---|---|---|---|---|---|---|---|---|---|
| | | | 20 | | | | | 25 | | | | | 30 | | |

| Gln | Thr | Glu | Pro | Tyr | Tyr | Asp | Met | Thr | Ser | Asn | Ala | Val | Leu | Thr | Phe |
|---|---|---|---|---|---|---|---|---|---|---|---|---|---|---|---|
| | | 35 | | | | | 40 | | | | | 45 | | | |

| Ile | Tyr | Phe | Val | Val | Cys | Val | Gly | Leu | Cys | Gly | Asn | Thr | Leu | Val |
|---|---|---|---|---|---|---|---|---|---|---|---|---|---|---|
| 50 | | | | | 55 | | | | | 60 | | | | |

```
Ile  Tyr  Val  Ile  Leu  Arg  Tyr  Ala  Lys  Met  Lys  Thr  Ile  Thr  Asn  Ile
 65                  70                   75                        80

Tyr  Ile  Leu  Asn  Leu  Ala  Ile  Ala  Asp  Glu  Leu  Phe  Met  Leu  Gly  Leu
                85                  90                        95

Pro  Phe  Leu  Ala  Met  Gln  Val  Ala  Leu  Val  His  Trp  Pro  Phe  Gly  Lys
               100                 105                      110

Ala  Ile  Cys  Arg  Val  Val  Met  Thr  Val  Asp  Gly  Ile  Asn  Gln  Phe  Thr
          115                 120                      125

Ser  Ile  Phe  Cys  Leu  Thr  Val  Met  Ser  Ile  Asp  Arg  Tyr  Leu  Ala  Val
          130                 135                 140

Val  His  Pro  Ile  Lys  Ser  Ala  Lys  Trp  Arg  Arg  Pro  Arg  Thr  Ala  Lys
145                 150                 155                           160

Met  Ile  Asn  Val  Ala  Val  Trp  Cys  Val  Ser  Leu  Leu  Val  Ile  Leu  Pro
                    165                 170                      175

Ile  Met  Ile  Tyr  Ala  Gly  Leu  Arg  Ser  Asn  Gln  Trp  Gly  Arg  Ser  Ser
               180                 185                      190

Cys  Thr  Ile  Asn  Trp  Pro  Gly  Glu  Ser  Gly  Ala  Trp  Tyr  Thr  Gly  Phe
          195                 200                      205

Ile  Ile  Tyr  Ala  Phe  Ile  Leu  Gly  Phe  Leu  Val  Pro  Leu  Thr  Ile  Ile
210                      215                      220

Cys  Leu  Cys  Tyr  Leu  Phe  Ile  Ile  Ile  Lys  Val  Lys  Ser  Ser  Gly  Ile
225                      230                 235                      240

Arg  Val  Gly  Ser  Ser  Lys  Arg  Lys  Lys  Ser  Glu  Lys  Lys  Val  Thr  Arg
               245                      250                      255

Met  Val  Ser  Ile  Val  Val  Ala  Val  Phe  Ile  Phe  Cys  Trp  Leu  Pro  Phe
               260                      265                      270

Tyr  Ile  Phe  Asn  Val  Ser  Ser  Val  Ser  Val  Ala  Ile  Ser  Pro  Thr  Pro
          275                      280                 285

Ala  Leu  Lys  Gly  Met  Phe  Asp  Phe  Val  Val  Ile  Leu  Thr  Tyr  Ala  Asn
290                      295                      300

Ser  Cys  Ala  Asn  Pro  Ile  Leu  Tyr  Ala  Phe  Leu  Ser  Asp  Asn  Phe  Lys
305                      310                      315                      320

Lys  Ser  Phe  Gln  Asn  Val  Leu  Cys  Leu  Val  Lys  Val  Ser  Gly  Thr  Glu
                325                      330                      335

Asp  Gly  Glu  Arg  Ser  Asp  Ser  Lys  Gln  Asp  Lys  Ser  Arg  Leu  Asn  Glu
               340                      345                 350

Thr  Thr  Glu  Thr  Gln  Arg  Thr  Leu  Leu  Asn  Gly  Asp  Leu  Gln  Thr  Ser
               355                 360                      365

Ile
```

( 2 ) INFORMATION FOR SEQ ID NO:9:

( i ) SEQUENCE CHARACTERISTICS:
       ( A ) LENGTH: 1296 base pairs
       ( B ) TYPE: nucleic acid
       ( C ) STRANDEDNESS: double
       ( D ) TOPOLOGY: linear ( i i ) MOLECULE TYPE: cDNA ( x i ) SEQUENCE DESCRIPTION: SEQ ID NO:9:

```
TGACTGCTGA- CCACCCTCCC CTCAGCCATG GACATGCTTC ATCCATCATC GGTGTCCACG        60

ACCTCAGAAC CTGAGAATGC CTCCTCGGCC TGGCCCCCAG ATGCCACCCT GGGCAACGTG       120

TCGGCGGGCC CAAGCCCGGC AGGGCTGGCC GTCAGTGGCG TTCTGATCCC CCTGGTCTAC       180

CTGGTGGTGT GCGTGGTGGG CCTGCTGGGT AACTCGCTGG TCATCTATGT GGTCCTGCGG       240

CACACGGCCA GCCCTTCAGT CACCAACGTC TACATCCTCA ACCTGGCGCT GGCCGACGAG       300
```

-continued

```
CTCTTCATGC TGGGGCTGCC CTTCCTGGCC GCCCAGAACG CCCTGTCCTA CTGGCCCTTC    360
GGCTCCCTCA TGTGCCGCCT GGTCATGGCG GTGGATGGCA TCAACCAGTT CACCAGCATA    420
TTCTGCCTGA CTGTCATGAG CGTGGACCGC TACCTGGCCG TGGTACATCC CACCCGCTCG    480
GCCCGCTGGC GCACAGCTCC GGTGGCCCGC ACGGTCAGCG CGGCTGTGTG GGTGGCCTCA    540
GCCGTGGTGG TGCTGCCCGT GGTGGTCTTC TCGGGAGTGC CCGCGGCAT GAGCACCTGC    600
CACATGCAGT GGCCCGAGCC GGCGGCGGCC TGGCGAGCCG GCTTCATCAT CTACACGGCC    660
GCACTGGGCT TCTTCGGGCC GCTGCTGGTC ATCTGCCTCT GCTACCTGCT CATCGTGGTG    720
AAGGTGCGCT CAGCTGGGCG CCGGGTGTGG GCACCCTCGT GCCAGCGGCG CCGGCGCTCC    780
GAACGCAGGG TCACGCGCAT GGTGGTGGCC GTGGTGGCGC TCTTCGTGCT CTGCTGGATG    840
CCCTTCTACG TGCTCAACAT CGTCAACGTG GTGTGCCCAC TGCCCGAGGA GCCTGCCTTC    900
TTTGGGCTCT ACTTCCTGGT GGTGGCGCTG CCCTATGCCA ACAGCTGTGC CAACCCCATC    960
CTTTATGGCT TCCTCTCCTA CCGCTTCAAG CAGGGCTTCC GCAGGGTCCT GCTGCGGCCC   1020
TCCCGCCGTG TGCGCAGCCA GGAGCCCACT GTGGGGCCCC CGGAGAAGAC TGAGGAGGAG   1080
GATGAGGAGG AGGAGGATGG GGAGGAGAGC AGGGAGGGGG GCAAGGGGAA GGAGATGAAC   1140
GGCCGGGTCA GCCAGATCAC GCAGCCTGGC ACCAGCGGGC AGGAGCGGCC GCCCAGCAGA   1200
GTGGCCAGCA AGGAGCAGCA GCTCCTACCC CAAGAGGCTT CCACTGGGGA GAAGTCCAGC   1260
ACGATGCGCA TCAGCTACCT GTAGGGGCCT GGGGAA                             1296
```

( 2 ) INFORMATION FOR SEQ ID NO:10:

( i ) SEQUENCE CHARACTERISTICS:
        ( A ) LENGTH: 418 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Asp Met Leu His Pro Ser Ser Val Ser Thr Thr Ser Glu Pro Glu
 1               5                  10                  15

Asn Ala Ser Ser Ala Trp Pro Pro Asp Ala Thr Leu Gly Asn Val Ser
            20                  25                  30

Ala Gly Pro Ser Pro Ala Gly Leu Ala Val Ser Gly Val Leu Ile Pro
        35                  40                  45

Leu Val Tyr Leu Val Val Cys Val Val Gly Leu Leu Gly Asn Ser Leu
    50                  55                  60

Val Ile Tyr Val Val Leu Arg His Thr Ala Ser Pro Ser Val Thr Asn
65                  70                  75                  80

Val Tyr Ile Leu Asn Leu Ala Leu Ala Asp Glu Leu Phe Met Leu Gly
                85                  90                  95

Leu Pro Phe Leu Ala Ala Gln Asn Ala Leu Ser Tyr Trp Pro Phe Gly
            100                 105                 110

Ser Leu Met Cys Arg Leu Val Met Ala Val Asp Gly Ile Asn Gln Phe
        115                 120                 125

Thr Ser Ile Phe Cys Leu Thr Val Met Ser Val Asp Arg Tyr Leu Ala
    130                 135                 140

Val Val His Pro Thr Arg Ser Ala Arg Trp Arg Thr Ala Pro Val Ala
145                 150                 155                 160

Arg Thr Val Ser Ala Ala Val Trp Val Ala Ser Ala Val Val Val Leu
                165                 170                 175

Pro Val Val Val Phe Ser Gly Val Pro Arg Gly Met Ser Thr Cys His
            180                 185                 190
```

```
Met Gln Trp Pro Glu Pro Ala Ala Ala Trp Arg Ala Gly Phe Ile Ile
    195             200                 205
Tyr Thr Ala Ala Leu Gly Phe Phe Gly Pro Leu Leu Val Ile Cys Leu
    210             215                 220
Cys Tyr Leu Leu Ile Val Val Lys Val Arg Ser Ala Gly Arg Arg Val
225             230                 235                 240
Trp Ala Pro Ser Cys Gln Arg Arg Arg Ser Glu Arg Arg Val Thr
                245                 250                 255
Arg Met Val Val Ala Val Val Ala Leu Phe Val Leu Cys Trp Met Pro
            260                 265                 270
Phe Tyr Val Leu Asn Ile Val Asn Val Val Cys Pro Leu Pro Glu Glu
        275                 280                 285
Pro Ala Phe Phe Gly Leu Tyr Phe Leu Val Val Ala Leu Pro Tyr Ala
    290                 295                 300
Asn Ser Cys Ala Asn Pro Ile Leu Tyr Gly Phe Leu Ser Tyr Arg Phe
305                 310                 315                 320
Lys Gln Gly Phe Arg Arg Val Leu Leu Arg Pro Ser Arg Arg Val Arg
                325                 330                 335
Ser Gln Glu Pro Thr Val Gly Pro Pro Glu Lys Thr Glu Glu Asp
            340                 345                 350
Glu Glu Glu Glu Asp Gly Glu Glu Ser Arg Glu Gly Gly Lys Gly Lys
            355                 360                 365
Glu Met Asn Gly Arg Val Ser Gln Ile Thr Gln Pro Gly Thr Ser Gly
    370                 375                 380
Gln Glu Arg Pro Pro Ser Arg Val Ala Ser Lys Glu Gln Gln Leu Leu
385                 390                 395                 400
Pro Gln Glu Ala Ser Thr Gly Glu Lys Ser Ser Thr Met Arg Ile Ser
                405                 410                 415
Tyr Leu
```

( 2 ) INFORMATION FOR SEQ ID NO:11:

( i ) SEQUENCE CHARACTERISTICS:
        ( A ) LENGTH: 1796 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:11:

```
ATCGGGCTCT GAGTTGGCAC ATAGTAGGTC TCTAAGTTCA AAGTGGCAGT GGTGTCCAGT      60
GTAGCACAGA GGAAGCATCT CTGTCACAAC TAAACTCTGT TCTTCCTCCT GTAGGTTACG     120
GTGGTTAGCT GCTGACTGAT CCTCATCTCA GCCATGGCCA CTGTTACCTA TCCCTCATCC     180
GAGCCTATGA CCTTGGACCC TGGGAACACA TCCTCGACCT GGCCCCTGGA TACCACCCTG     240
GGGAACACAT CCGCTGGCGC TAGCCTGACA GGCCTGGCTG TCAGTGGCAT CTTGATCTCT     300
CTGGTGTACC TGGTGGTGTG CGTGGTGGGT CTGCTGGGCA ACTCGCTGGT GATCTACGTG     360
GTCCTGCGGC ACACGTCCAG CCCATCAGTG ACCAGTGTCT ATATCCTCAA CCTGGCTCTG     420
GCTGATGAGC TCTTCATGCT AGGGCTACCC TTCCTGGCTG CTCAGAACGC CCTGTCCTAC     480
TGGCCCTTTG GATCTCTCAT GTGCCGTCTG GTCATGGCCG TGGATGGCAT CAACCAGTTC     540
ACCAGCATCT TCTGCCTCAC CGTCATGAGT GTGGACCGCT ATCTGGCTGT GGTGCACCCC     600
ACACGCTCAG CCCGCTGGCG CACGGCACCA GTGGCTCGCA CGGTCAGTCG AGCTGTCTGG     660
GTGGCCTCGG CTGTGGTGGT GCTGCCTGTG GTTGTGTTCT CAGGAGTGCC CCGGGGCATG     720
```

| | | | | |
|---|---|---|---|---|
| AGCACGTGCC | ACATGCAGTG | GCCAGAGCCA | GCGGCTGCCT | GGCGAACAGC | CTTTATCATC | 780 |
| TACATGGCCG | CACTGGGCTT | CTTTGGGCCC | CTGCTGGTCA | TCTGCTTGTG | CTACTTGCTC | 840 |
| ATTGTGGTAA | AGGTGCGGTC | GACCACCCGG | CGGGTGCGGG | CGCCCTCGTG | TCAGTGGGTA | 900 |
| CAGGCACCCG | CATGCCAGCG | GCGACGCCGC | TCTGAGCGCA | GGGTCACACG | CATGGTGGTG | 960 |
| GCCGTGGTGG | CACTCTTCGT | CCTCTGCTGG | ATGCCTTTCT | ATCTGCTCAA | CATCGTCAAT | 1020 |
| GTGGTGTGCC | CGCTGCCGGA | GGAGCCTGCC | TTCTTCGGCC | TCTACTTCCT | GGTGGTGGCG | 1080 |
| CTGCCCTATG | CCAACAGCTG | CGCAAACCCC | ATCCTCTACG | GCTTCCTCTC | CTACCGCTTC | 1140 |
| AAGCAGGGCT | TTCGCAGGAT | CCTGCTAAGA | CCATCACGTC | GCATTCGGAG | CCAGGAGCCA | 1200 |
| GGGTCGGGAC | CTCCAGAGAA | GACTGAAGAG | GAGGAGGATG | AAGAAGAAGA | AGAGAGAAGG | 1260 |
| GAAGAGGAGG | AGCGGAGGAT | GCAGAGAGGG | CAGGAGATGA | ACGGGAGGCT | CAGTCAGATC | 1320 |
| GCACAGGCTG | GCACTAGTGG | ACAACAGCCA | CGGCCCTGCA | CAGGGACTGC | TAAGGAGCAG | 1380 |
| CAGCTTCTGC | CCCAGGAGGC | CACAGCTGGG | GACAAGGCCA | GCACACTGAG | CCATCTGTAA | 1440 |
| GGACCTTCAA | AGAACCAGCG | TGGTTCAGAA | AAGAGCAGAA | GCTGGGCTTG | ACCTCGGGGC | 1500 |
| TCGAACACCC | ACATGCAGTG | ATCTGAGCAG | CAGCGAGAAT | GACCTTATGT | ACATGGCTGT | 1560 |
| CCTGGTCCTC | TCTGGACCGC | TGTGGTACCA | GGGTCCAGTG | ATGGAATGTT | TATAGGCTTG | 1620 |
| AACTCTGTGC | CACTGTGCCA | GGACTTGCTG | TGTGTCCTTT | GGCCGGTCAT | TTACCCTTTC | 1680 |
| TGGGCCTTGT | TTTCTTCTTT | TGACTCAGGG | ATGGGTAAAC | TGAGCCTGGA | TGGGCCCTGT | 1740 |
| CAGAAGAGGG | GTCTGGAATC | CTTACCAGGA | TCACTCTCCT | TTCAGATCGA | GTCGAC | 1796 |

( 2 ) INFORMATION FOR SEQ ID NO:12:

( i ) SEQUENCE CHARACTERISTICS:
   ( A ) LENGTH: 428 amino acids
   ( B ) TYPE: amino acid
   ( D ) TOPOLOGY: linear ( i i ) MOLECULE TYPE: protein ( x i ) SEQUENCE DESCRIPTION: SEQ ID NO:12:

```
Met Ala Thr Val Thr Tyr Pro Ser Ser Glu Pro Met Thr Leu Asp Pro
 1               5                  10                  15

Gly Asn Thr Ser Ser Thr Trp Pro Leu Asp Thr Thr Leu Gly Asn Thr
                20                  25                  30

Ser Ala Gly Ala Ser Leu Thr Gly Leu Ala Val Ser Gly Ile Leu Ile
            35                  40                  45

Ser Leu Val Tyr Leu Val Val Cys Val Val Gly Leu Leu Gly Asn Ser
        50                  55                  60

Leu Val Ile Tyr Val Val Leu Arg His Thr Ser Ser Pro Ser Val Thr
65                  70                  75                  80

Ser Val Tyr Ile Leu Asn Leu Ala Leu Ala Asp Glu Leu Phe Met Leu
                85                  90                  95

Gly Leu Pro Phe Leu Ala Ala Gln Asn Ala Leu Ser Tyr Trp Pro Phe
            100                 105                 110

Gly Ser Leu Met Cys Arg Leu Val Met Ala Val Asp Gly Ile Asn Gln
        115                 120                 125

Phe Thr Ser Ile Phe Cys Leu Thr Val Met Ser Val Asp Arg Tyr Leu
130                 135                 140

Ala Val Val His Pro Thr Arg Ser Ala Arg Trp Arg Thr Ala Pro Val
145                 150                 155                 160

Ala Arg Thr Val Ser Arg Ala Val Trp Val Ala Ser Ala Val Val Val
                165                 170                 175

Leu Pro Val Val Val Phe Ser Gly Val Pro Arg Gly Met Ser Thr Cys
```

|     |     |     | 180 |     |     |     |     | 185 |     |     |     | 190 |     |     |
| --- | --- | --- | --- | --- | --- | --- | --- | --- | --- | --- | --- | --- | --- | --- |
| His | Met | Gln<br>195 | Trp | Pro | Glu | Pro | Ala<br>200 | Ala | Ala | Trp | Arg | Thr<br>205 | Ala | Phe | Ile |
| Ile | Tyr<br>210 | Met | Ala | Ala | Leu | Gly<br>215 | Phe | Phe | Gly | Pro | Leu<br>220 | Leu | Val | Ile | Cys |
| Leu<br>225 | Cys | Tyr | Leu | Leu | Ile<br>230 | Val | Val | Lys | Val | Arg<br>235 | Ser | Thr | Thr | Arg | Arg<br>240 |
| Val | Arg | Ala | Pro | Ser<br>245 | Cys | Gln | Trp | Val | Gln<br>250 | Ala | Pro | Ala | Cys | Gln<br>255 | Arg |
| Arg | Arg | Arg | Ser<br>260 | Glu | Arg | Arg | Val | Thr<br>265 | Arg | Met | Val | Val | Ala<br>270 | Val | Val |
| Ala | Leu | Phe<br>275 | Val | Leu | Cys | Trp | Met<br>280 | Pro | Phe | Tyr | Leu | Leu<br>285 | Asn | Ile | Val |
| Asn | Val<br>290 | Val | Cys | Pro | Leu | Pro<br>295 | Glu | Glu | Pro | Ala | Phe<br>300 | Phe | Gly | Leu | Tyr |
| Phe<br>305 | Leu | Val | Val | Ala | Leu<br>310 | Pro | Tyr | Ala | Asn | Ser<br>315 | Cys | Ala | Asn | Pro | Ile<br>320 |
| Leu | Tyr | Gly | Phe | Leu<br>325 | Ser | Tyr | Arg | Phe | Lys<br>330 | Gln | Gly | Phe | Arg | Arg<br>335 | Ile |
| Leu | Leu | Arg | Pro<br>340 | Ser | Arg | Arg | Ile | Arg<br>345 | Ser | Gln | Glu | Pro | Gly<br>350 | Ser | Gly |
| Pro | Pro | Glu<br>355 | Lys | Thr | Glu | Glu | Glu<br>360 | Glu | Asp | Glu | Glu | Glu<br>365 | Glu | Glu | Arg |
| Arg | Glu<br>370 | Glu | Glu | Glu | Arg | Arg<br>375 | Met | Gln | Arg | Gly | Gln<br>380 | Glu | Met | Asn | Gly |
| Arg<br>385 | Leu | Ser | Gln | Ile | Ala<br>390 | Gln | Ala | Gly | Thr | Ser<br>395 | Gly | Gln | Gln | Pro | Arg<br>400 |
| Pro | Cys | Thr | Gly | Thr<br>405 | Ala | Lys | Glu | Gln | Gln<br>410 | Leu | Leu | Pro | Gln | Glu<br>415 | Ala |
| Thr | Ala | Gly | Asp<br>420 | Lys | Ala | Ser | Thr | Leu<br>425 | Ser | His | Leu |     |     |     |     |

What is claimed is:

1. A recombinant vector incorporating a DNA segment encoding a somatostatin receptor polypeptide, said DNA segment being selected from the group consisting of:
   (a) a DNA having a sequence encoding a somatostatin receptor polypeptide having an amino acid sequence selected from the group consisting of Sequence ID Numbers 2, 4, 6, 10 and 12; and
   (b) a DNA which is hybridizable to a DNA having a nucleotide sequence selected from the group consisting of Sequence ID Numbers 1, 3, 5, 7, 9 and 11 under standard hybridization conditions.

2. The vector of claim 1, wherein the amino acid sequence of the encoded somatostatin receptor polypeptide is selected from the group of somatostatin receptor polypeptide sequences consisting of:
   (a) amino acids 1 to 391 of Sequence ID number 2;
   (b) amino acids 1 to 391 of Sequence ID number 4;
   (c) amino acids 1 to 369 of Sequence ID number 6;
   (d) amino acids 1 to 369 of Sequence ID number 8;
   (e) amino acids 1 to 418 of Sequence ID number 10; and
   (f) amino acids 1 to 428 of Sequence ID number 12.

3. The vector of claim 1, where the somatostatin receptor polypeptide encoding sequence is positioned adjacent to and under the control of an effective promoter.

4. The vector of claim 3, where the promotor comprises a prokaryotic promoter, the vector being adapted for expression in prokaryotic host.

5. The vector of claim 3, where the promoter comprises a eukaryotic promoter, the vector being adapted for expression in a eukaryotic host, and the vector further includes a polyadenylation signal position 3' of the carboxy-terminal amino acid, and within a transcriptional unit of the encoded polypeptide.

6. The recombinant vector of claim 1 wherein the DNA segment encodes a somatostatin receptor corresponding to the polypeptide of Sequence ID number 2.

7. The recombinant vector of claim 6 wherein the DNA segment is represented by Sequence ID number 1.

8. The recombinant vector of claim 1 wherein the DNA segment encodes a somatostatin receptor corresponding to the polypeptide of Sequence ID number 4.

9. The recombinant vector of claim 8 wherein the DNA segment is represented by Sequence ID number 3.

10. The recombinant vector of claim 1 wherein the DNA segment encodes a somatostatin receptor corresponding to the polypeptide of Sequence ID number 6.

11. The recombinant vector of claim 10 wherein the DNA segment is represented by Sequence ID number 5.

12. The recombinant vector of claim 1 wherein the DNA segment encodes a somatostatin receptor corresponding to the polypeptide of Sequence ID number 8.

13. The recombinant vector of claim 12 wherein the DNA segment is represented by Sequence ID number 7.

14. The recombinant vector of claim 1 wherein the DNA segment encodes a somatostatin receptor corresponding to the polypeptide of Sequence ID number 10.

15. The recombinant vector of claim 14 wherein the DNA segment is represented by Sequence ID number 9.

16. The recombinant vector of claim 1 wherein the DNA segment encodes a somatostatin receptor corresponding to the polypeptide of Sequence ID number 12.

17. The recombinant vector of claim 16 wherein the DNA segment is represented by Sequence ID number 11.

18. An isolated DNA segment having a sequence encoding a somatostatin receptor polypeptide wherein the segment is hybridizable to a DNA segment having a nucleotide sequence selected from the group consisting of Sequence ID Numbers 1, 3, 5, 7, 9 and 11 under standard hybridization conditions.

19. The isolated DNA segment of claim 18, wherein the amino acid sequence of the encoded somatostatin receptor polypeptide is selected from the group of somatostatin polypeptide sequences consisting of:
(a) amino acids 1 to 391 of Sequence ID number 2;
(b) amino acids 1 to 391 of Sequence ID number 4;
(c) amino acids 1 to 369 of Sequence ID number 6;
(d) amino acids 1 to 369 of Sequence ID number 8;
(e) amino acids 1 to 418 of Sequence ID number 10; and
(f) amino acids 1 to 428 of Sequence ID number 12.

20. A recombinant host cell which incorporates an isolated DNA segment in accordance with claim 18 or 19.

21. A recombinant host cell of claim 20 where the DNA segment encoding a somatostatin receptor polypeptide is under the transcriptional control of regulatory signals functional in the recombinant host cell which regulatory signals appropriately control the expression of the somatostatin receptor polypeptide in a manner to allow all necessary transcriptional and post transcriptional modification.

22. An isolated DNA segment comprising a sequence region consisting of at least 14 contiguous bases that are complementary to, or have the same sequence as, at least 14 contiguous bases of a DNA sequence selected from the group consisting of Sequence ID Numbers 1, 3, 5, 7, 9 and 11.

23. The isolated DNA segment of claim 22, where the sequence comprises at least a 20 contiguous base sequence of a DNA sequence selected from the group consisting of Sequence ID Numbers 1, 3, 5, 7, 9 and 11.

24. The isolated DNA segment of claim 22, where the sequence comprises at least a 30 contiguous base sequence of a DNA sequence selected from the group consisting of Sequence ID Numbers 1, 3, 5, 7, 9 and 11.

25. The isolated DNA segment of claim 22, where the sequence comprises at least a 40 contiguous base sequence of a DNA sequence selected from the group consisting of Sequence ID Numbers 1, 3, 5, 7, 9 and 11.

26. The isolated DNA segment of claim 22, further defined as encoding a somatostatin receptor polypeptide.

27. A recombinant vector incorporating a DNA segment as defined by any one of claims 18, 19 and 22–24.

28. A recombinant eukaryotic host cell which incorporates an isolated DNA segment in accordance with claim 18 or 22.

29. The recombinant host cell of claim 28, further defined as a yeast cell.

30. A recombinant prokaryotic host cell which incorporates an isolated DNA segment in accordance with claim 18 or 22.

31. The DNA segment of claim 22, further defined as comprising a sequence region consisting of at least 20 contiguous bases that are complementary to, or have the same sequence as, at least 20 contiguous bases of Sequence ID number 1.

32. The DNA segment of claim 31, further defined as comprising a sequence region consisting of at least 30 contiguous bases that are complementary to, or have the same sequence as, at least 30 contiguous bases of Sequence ID number 1.

33. The DNA segment of claim 22, further defined as comprising a sequence region consisting of at least 20 contiguous bases that are complementary to, or have the same sequence as, at least 20 contiguous bases of Sequence ID number 3.

34. The DNA segment of claim 33, further defined as comprising a sequence region consisting of at least 30 contiguous bases that are complementary to, or have the same sequence as, at least 30 contiguous bases of Sequence ID number 3.

35. The DNA segment of claim 22, further defined as comprising a sequence region consisting of at least 20 contiguous bases that are complementary to, or have the same sequence as, at least 20 contiguous bases of Sequence ID number 5.

36. The DNA segment of claim 35, further defined as comprising a sequence region consisting of at least 30 contiguous bases that are complementary to, or have the same sequence as, at least 30 contiguous bases of Sequence ID number 5.

37. The DNA segment of claim 22, further defined as comprising a sequence region consisting of at least 20 contiguous bases that are complementary to, or have the same sequence as, at least 20 contiguous bases of Sequence ID number 7.

38. The DNA segment of claim 37, further defined as comprising a sequence region consisting of at least 30 contiguous bases that are complementary to, or have the same sequence as, at least 30 contiguous bases of Sequence ID number 7.

39. The DNA segment of claim 22, further defined as comprising a sequence region consisting of at least 20 contiguous bases that are complementary to, or have the same sequence as, at least 20 contiguous bases of Sequence ID number 9.

40. The DNA segment of claim 39, further defined as comprising a sequence region consisting of at least 30 contiguous bases that are complementary to, or have the same sequence as, at least 30 contiguous bases of Sequence ID number 9.

41. The DNA segment of claim 22, further defined as comprising a sequence region consisting of at least 20 contiguous bases that are complementary to, or have the same sequence as, at least 20 contiguous bases of Sequence ID number 11.

42. The DNA segment of claim 41, further defined as comprising a sequence region consisting of at least 30 contiguous bases that are complementary to, or have the same sequence as, at least 30 contiguous bases of Sequence ID number 11.

* * * * *

UNITED STATES PATENT AND TRADEMARK OFFICE
CERTIFICATE OF CORRECTION

PATENT NO. : 5,436,155
DATED : July 25, 1995
INVENTOR(S) : Bell et al.

It is certified that error appears in the above-indentified patent and that said Letters Patent is hereby corrected as shown below:

In claim 21, column 53, line 41, delete "A" and insert --The-- therefor.

In claim 20, column 53, line 40, delete "19" and insert --26-- therefor.

Signed and Sealed this

Thirty-first Day of October 1995

Attest:

BRUCE LEHMAN

Attesting Officer        Commissioner of Patents and Trademarks